(12) United States Patent
Riggs et al.

(10) Patent No.: US 8,623,615 B2
(45) Date of Patent: *Jan. 7, 2014

(54) SOLUBILIZATION AND PURIFICATION OF A TARGET PROTEIN FUSED TO A MUTANT MALTOSE-BINDING PROTEIN

(75) Inventors: Paul Riggs, Hooksett, NH (US); Iris Walker, Rowley, MA (US); Paul A. Colussi, Gloucester, MA (US); Mehul Ganatra, Gloucester, MA (US); Christopher H. Taron, Essex, MA (US)

(73) Assignee: New England Biolabs, Inc., Ipswich, MA (US)

( * ) Notice: Subject to any disclaimer, the term of this patent is extended or adjusted under 35 U.S.C. 154(b) by 51 days.

This patent is subject to a terminal disclaimer.

(21) Appl. No.: 13/259,837

(22) PCT Filed: Apr. 1, 2009

(86) PCT No.: PCT/US2009/039111
§ 371 (c)(1),
(2), (4) Date: Sep. 23, 2011

(87) PCT Pub. No.: WO2010/114532
PCT Pub. Date: Oct. 7, 2010

(65) Prior Publication Data
US 2012/0028305 A1      Feb. 2, 2012

(51) Int. Cl.
*C12P 21/06* (2006.01)
*C07K 14/00* (2006.01)
*C07H 21/02* (2006.01)

(52) U.S. Cl.
USPC .......................... 435/69.1; 530/350; 536/23.1

(58) Field of Classification Search
USPC .......................... 435/69.1; 530/350; 536/23.1
See application file for complete search history.

(56) References Cited

U.S. PATENT DOCUMENTS 5,643,758 A       7/1997   Guan et al.

FOREIGN PATENT DOCUMENTS

WO      2007/120809 A1      10/2007

OTHER PUBLICATIONS

Kapust & Waugh, Protein Sci. 8:1668-74 (1999).
Spurlino et al., J. Biol. Chem. 266:5202-5219 (1991).
Marvin et al., Nature Structural Biology 8:795-798 (2001).
Telmer & Shilton, Journal of Biol. Chem. 278:34555-34567 (2003).
Uy and Wold, Anal. Biochem. 81:98-107 (1977).
Fox et al., FEBS Lett. 537:53-57 (2003).
Fromant et al., Analytical Biochemistry 224: 347-353 (1995).
Guan et al., Nucleic Acid Research, 33:6225-6234 (2005).

*Primary Examiner* — Karen Cochrane Carlson
(74) *Attorney, Agent, or Firm* — New England Biolabs, Inc; Harriet M. Strimpel

(57) ABSTRACT

Methods and compositions are provided that relate to a composition that includes a modified maltose-binding protein (MBP) which when fused to a protein results in an increase in binding affinity for maltodextrin compared with the wild type MBP fused to the protein, the modified MBP maintaining enhanced solubility. The modification includes a mutation selected from the group consisting of: F68L, I318V, Q326R, V344M, and $T_{372}TTTITITTTLGIEGR_{387}$ or consists of two or more mutations selected from the group consisting of: F68L, S146T, A313V, I318V, I318A, Q326R, V344M and $T_{372}TTTITITTTLGIEGR_{387}$ mutants.

15 Claims, 26 Drawing Sheets

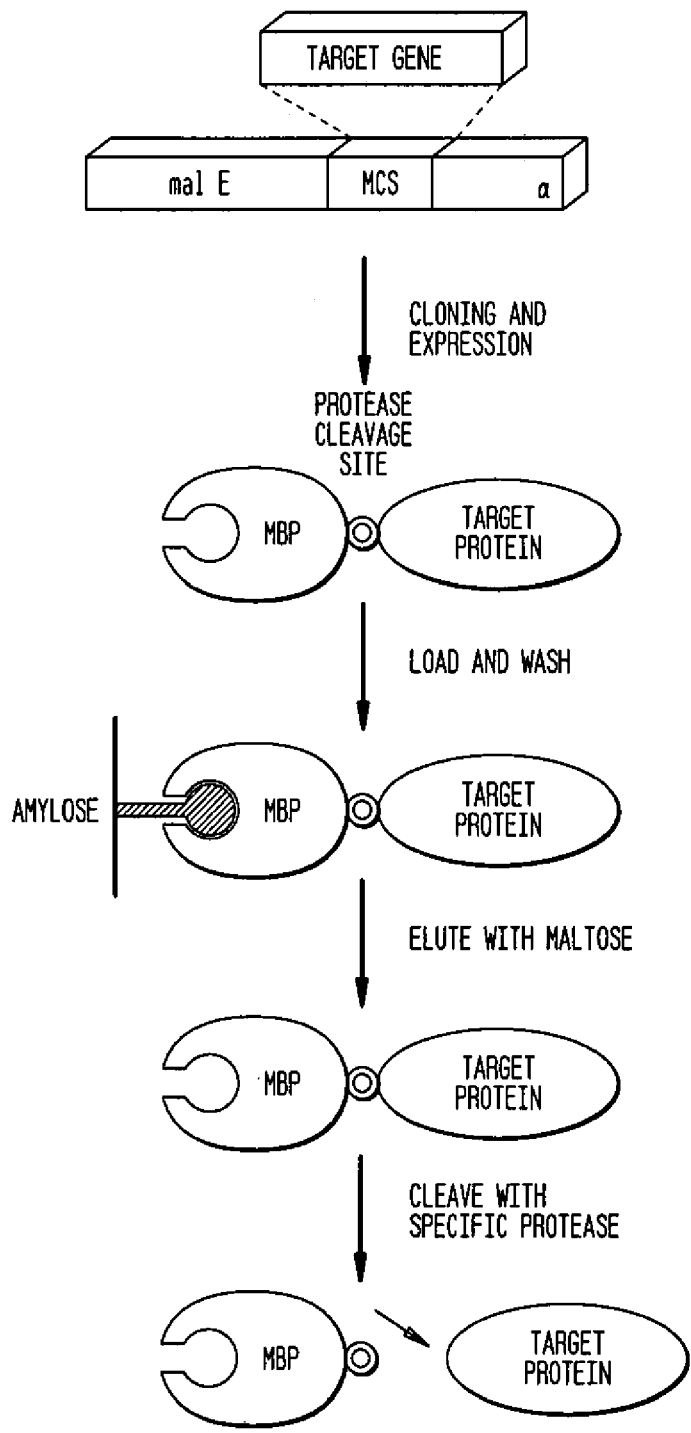

FIG. 2A-1
wild type MBP (SEQ ID NOS:1 and 2)

```
1501 ----------+----------+----------+----------+----------+----------+ 1560
     GCACTTCACCAACAAGGACCATAGCATATGAAAATCGAAGAAGGTAAACTGGTAATCTGG
                                   M  K  I  E  E  G  K  L  V  I  W

1561 ----------+----------+----------+----------+----------+----------+ 1620
     ATTAACGGCGATAAAGGCTATAACGGTCTCGCTGAAGTCGGTAAGAAATTCGAGAAAGAT
      I  N  G  D  K  G  Y  N  G  L  A  E  V  G  K  K  F  E  K  D

1621 ----------+----------+----------+----------+----------+----------+ 1680
     ACCGGAATTAAAGTCACCGTTGAGCATCCGGATAAACTGGAAGAGAAATTCCCACAGGTT
      T  G  I  K  V  T  V  E  H  P  D  K  L  E  E  K  F  P  Q  V

1681 ----------+----------+----------+----------+----------+----------+ 1740
     GCGGCAACTGGCGATGGCCCTGACATTATCTTCTGGGCACACGACCGCTTTGGTGGCTAC
      A  A  T  G  D  G  P  D  I  I  F  W  A  H  D  R  F  G  G  Y

1741 ----------+----------+----------+----------+----------+----------+ 1800
     GCTCAATCTGGCCTGTTGGCTGAAATCACCCCCGGACAAAGCGTTCCAGGACAAGCTGTAT
      A  Q  S  G  L  L  A  E  I  T  P  D  K  A  F  Q  D  K  L  Y

1801 ----------+----------+----------+----------+----------+----------+ 1860
     CCGTTTACCTGGGATGCCGTACGTTACAACGGCAAGCTGATTGCTTACCCGATCGCTGTT
      P  F  T  W  D  A  V  R  Y  N  G  K  L  I  A  Y  P  I  A  V

1861 ----------+----------+----------+----------+----------+----------+ 1920
     GAAGCGTTATCGCTGATTTATAACAAAGATCTGCTGCCGAACCCGCCAAAAACCTGGGAA
      E  A  L  S  L  I  Y  N  K  D  L  L  P  N  P  P  K  T  W  E

1921 ----------+----------+----------+----------+----------+----------+ 1980
     GAGATCCCGGCGCTGGATAAAGAACTGAAAGCGAAAGGTAAGAGCGCGCTGATGTTCAAC
      E  I  P  A  L  D  K  E  L  K  A  K  G  K  S  A  L  M  F  N

1981 ----------+----------+----------+----------+----------+----------+ 2040
     CTGCAAGAACCGTACTTCACCTGGCCGCTGATTGCTGCTGACGGGGGTTATGCGTTCAAG
      L  Q  E  P  Y  F  T  W  P  L  I  A  A  D  G  G  Y  A  F  K

2041 ----------+----------+----------+----------+----------+----------+ 2100
     TATGAAAACGGCAAGTACGACATTAAAGACGTGGGCGTGGATAACGCTGGCGCGAAAGCG
      Y  E  N  G  K  Y  D  I  K  D  V  G  V  D  N  A  G  A  K  A
```

FIG. 2A-2
wild type MBP

```
2101 ----------+----------+----------+----------+----------+----------+ 2160
     GGTCTGACCTTCCTGGTTGACCTGATTAAAAACAAACACATGAATGCAGACACCGATTAC
      G  L  T  F  L  V  D  L  I  K  N  K  H  M  N  A  D  T  D  Y

2161 ----------+----------+----------+----------+----------+----------+ 2220
     TCCATCGCAGAAGCTGCCTTTAATAAAGGCGAAACAGCGATGACCATCAACGGCCCGTGG
      S  I  A  E  A  A  F  N  K  G  E  T  A  M  T  I  N  G  P  W

2221 ----------+----------+----------+----------+----------+----------+ 2280
     GCATGGTCCAACATCGACACCAGCAAAGTGAATTATGGTGTAACGGTACTGCCGACCTTC
      A  W  S  N  I  D  T  S  K  V  N  Y  G  V  T  V  L  P  T  F

2281 ----------+----------+----------+----------+----------+----------+ 2340
     AAGGGTCAACCATCCAAACCGTTCGTTGGCGTGCTGAGCGCAGGTATTAACGCCGCCAGT
      K  G  Q  P  S  K  P  F  V  G  V  L  S  A  G  I  N  A  A  S

2341 ----------+----------+----------+----------+----------+----------+ 2400
     CCGAACAAAGAGCTGGCAAAAGAGTTCCTCGAAAACTATCTGCTGACTGATGAAGGTCTG
      P  N  K  E  L  A  K  E  F  L  E  N  Y  L  L  T  D  E  G  L

2401 ----------+----------+----------+----------+----------+----------+ 2460
     GAAGCGGTTAATAAAGACAAACCGCTGGGTGCCGTAGCGCTGAAGTCTTACGAGGAAGAG
      E  A  V  N  K  D  K  P  L  G  A  V  A  L  K  S  Y  E  E  E

2461 ----------+----------+----------+----------+----------+----------+ 2520
     TTGGCGAAAGATCCACGTATTGCCGCCACTATGGAAAACGCCCAGAAAGGTGAAATCATG
      L  A  K  D  P  R  I  A  A  T  M  E  N  A  Q  K  G  E  I  M

2521 ----------+----------+----------+----------+----------+----------+ 2580
     CCGAACATCCCGCAGATGTCCGCTTTCTGGTATGCCGTGCGTACTGCGGTGATCAACGCC
      P  N  I  P  Q  M  S  A  F  W  Y  A  V  R  T  A  V  I  N  A

2581 ----------+----------+----------+----------+----------+----------+ 2640
     GCCAGCGGTCGTCAGACTGTCGATGAAGCCCTGAAAGACGCGCAGACTAATTCGAGCTCG
      A  S  G  R  Q  T  V  D  E  A  L  K  D  A  Q  T  N  S  S  S

2641 ----------+----------+----------+---------+-------- 2688
     AACAACAACAACAATAACAATAACAACAACCTCGGGATCGAGGGAAGG
      N  N  N  N  N  N  N  N  N  L  G  I  E  G  R
```

FIG. 2B-1
A313V Mutant (SEQ ID NOS:3 and 4)

```
1501 ----------+---------+----------+----------+----------+---------+ 1560
     GCACTTCACCAACAAGGACCATAGCATATGAAAATCGAAGAAGGTAAACTGGTAATCTGG
                                 M  K  I  E  E  G  K  L  V  I  W

1561 ----------+---------+----------+----------+----------+---------+ 1620
     ATTAACGGCGATAAAGGCTATAACGGTCTCGCTGAAGTCGGTAAGAAATTCGAGAAAGAT
      I  N  G  D  K  G  Y  N  G  L  A  E  V  G  K  K  F  E  K  D

1621 ----------+---------+----------+----------+----------+---------+ 1680
     ACCGGAATTAAAGTCACCGTTGAGCATCCGGATAAACTGGAAGAGAAATTCCCACAGGTT
      T  G  I  K  V  T  V  E  H  P  D  K  L  E  E  K  F  P  Q  V

1681 ----------+---------+----------+----------+----------+---------+ 1740
     GCGGCAACTGGCGATGGCCCTGACATTATCTTCTGGGCACACGACCGCTTTGGTGGCTAC
      A  A  T  G  D  G  P  D  I  I  F  W  A  H  D  R  F  G  G  Y

1741 ----------+---------+----------+----------+----------+---------+ 1800
     GCTCAATCTGGCCTGTTGGCTGAAATCACCCCGGACAAAGCGTTCCAGGACAAGCTGTAT
      A  Q  S  G  L  L  A  E  I  T  P  D  K  A  F  Q  D  K  L  Y

1801 ----------+---------+----------+----------+----------+---------+ 1860
     CCGTTTACCTGGGATGCCGTACGTTACAACGGCAAGCTGATTGCTTACCCGATCGCTGTT
      P  F  T  W  D  A  V  R  Y  N  G  K  L  I  A  Y  P  I  A  V

1861 ----------+---------+----------+----------+----------+---------+ 1920
     GAAGCGTTATCGCTGATTTATAACAAAGATCTGCTGCCGAACCCGCCAAAAACCTGGGAA
      E  A  L  S  L  I  Y  N  K  D  L  L  P  N  P  P  K  T  W  E

1921 ----------+---------+----------+----------+----------+---------+ 1980
     GAGATCCCGGCGCTGGATAAAGAACTGAAAGCGAAAGGTAAGAGCGCGCTGATGTTCAAC
      E  I  P  A  L  D  K  E  L  K  A  K  G  K  S  A  L  M  F  N

1981 ----------+---------+----------+----------+----------+---------+ 2040
     CTGCAAGAACCGTACTTCACCTGGCCGCTGATTGCTGCTGACGGGGGTTATGCGTTCAAG
      L  Q  E  P  Y  F  T  W  P  L  I  A  A  D  G  G  Y  A  F  K

2041 ----------+---------+----------+----------+----------+---------+ 2100
     TATGAAAACGGCAAGTACGACATTAAAGACGTGGGCGTGGATAACGCTGGCGCGAAAGCG
      Y  E  N  G  K  Y  D  I  K  D  V  G  V  D  N  A  G  A  K  A
```

FIG. 2B-2
A313V Mutant

```
2101 ----------+----------+----------+----------+----------+----------+ 2160
     GGTCTGACCTTCCTGGTTGACCTGATTAAAAACAAACACATGAATGCAGACACCGATTAC
      G  L  T  F  L  V  D  L  I  K  N  K  H  M  N  A  D  T  D  Y

2161 ----------+----------+----------+----------+----------+----------+ 2220
     TCCATCGCAGAAGCTGCCTTTAATAAAGGCGAAACAGCGATGACCATCAACGGCCCGTGG
      S  I  A  E  A  A  F  N  K  G  E  T  A  M  T  I  N  G  P  W

2221 ----------+----------+----------+----------+----------+----------+ 2280
     GCATGGTCCAACATCGACACCAGCAAAGTGAATTATGGTGTAACGGTACTGCCGACCTTC
      A  W  S  N  I  D  T  S  K  V  N  Y  G  V  T  V  L  P  T  F

2281 ----------+----------+----------+----------+----------+----------+ 2340
     AAGGGTCAACCATCCAAACCGTTCGTTGGCGTGCTGAGCGCAGGTATTAACGCCGCCAGT
      K  G  Q  P  S  K  P  F  V  G  V  L  S  A  G  I  N  A  A  S

2341 ----------+----------+----------+----------+----------+----------+ 2400
     CCGAACAAAGAGCTGGCAAAAGAGTTCCTCGAAAACTATCTGCTGACTGATGAAGGTCTG
      P  N  K  E  L  A  K  E  F  L  E  N  Y  L  L  T  D  E  G  L

2401 ----------+----------+----------+----------+----------+----------+ 2460
     GAAGCGGTTAATAAAGACAAACCGCTGGGTGCCGTAGCGCTGAAGTCTTACGAGGAAGAG
      E  A  V  N  K  D  K  P  L  G  A  V  A  L  K  S  Y  E  E  E

2461 ----------+----------+----------+----------+----------+----------+ 2520
     TTGGTGAAAGATCCACGTATTGCCGCCACTATGGAAAACGCCCAGAAAGGTGAAATCATG
      L  V  K  D  P  R  I  A  A  T  M  E  N  A  Q  K  G  E  I  M

2521 ----------+----------+----------+----------+----------+----------+ 2580
     CCGAACATCCCGCAGATGTCCGCTTTCTGGTATGCCGTGCGTACTGCGGTGATCAACGCC
      P  N  I  P  Q  M  S  A  F  W  Y  A  V  R  T  A  V  I  N

2581 ----------+----------+----------+----------+----------+----------+ 2640
     GCCAGCGGTCGTCAGACTGTCGATGAAGCCCTGAAAGACGCGCAGACTAATTCGAGCTCG
      A  S  G  R  Q  T  V  D  E  A  L  K  D  A  Q  T  N  S  S  S

2641 ----------+----------+----------+---------+--------- 2688
     AACAACAACAACAATAACAATAACAACAACCTCGGGATCGAGGGAAGG
      N  N  N  N  N  N  N  N  N  N  L  G  I  E  G  R
```

FIG. 2C-1
S146T Mutant (SEQ ID NOS:5 and 6)

```
1501 ----------+----------+----------+----------+----------+----------+ 1560
     GCACTTCACCAACAAGGACCATAGCATATGAAAATCGAAGAAGGTAAACTGGTAATCTGG
                                   M  K  I  E  E  G  K  L  V  I  W

1561 ----------+----------+----------+----------+----------+----------+ 1620
     ATTAACGGCGATAAAGGCTATAACGGTCTCGCTGAAGTCGGTAAGAAATTCGAGAAAGAT
      I  N  G  D  K  G  Y  N  G  L  A  E  V  G  K  K  F  E  K  D

1621 ----------+----------+----------+----------+----------+----------+ 1680
     ACCGGAATTAAAGTCACCGTTGAGCATCCGGATAAACTGGAAGAGAAATTCCCACAGGTT
      T  G  I  K  V  T  V  E  H  P  D  K  L  E  E  K  F  P  Q  V

1681 ----------+----------+----------+----------+----------+----------+ 1740
     GCGGCAACTGGCGATGGCCCTGACATTATCTTCTGGGCACACGACCGCTTTGGTGGCTAC
      A  A  T  G  D  G  P  D  I  I  F  W  A  H  D  R  F  G  G  Y

1741 ----------+----------+----------+----------+----------+----------+ 1800
     GCTCAATCTGGCCTGTTGGCTGAAATCACCCCGGACAAAGCGTTCCAGGACAAGCTGTAT
      A  Q  S  G  L  L  A  E  I  T  P  D  K  A  F  Q  D  K  L  Y

1801 ----------+----------+----------+----------+----------+----------+ 1860
     CCGTTTACCTGGGATGCCGTACGTTACAACGGCAAGCTGATTGCTTACCCGATCGCTGTT
      P  F  T  W  D  A  V  R  Y  N  G  K  L  I  A  Y  P  I  A  V

1861 ----------+----------+----------+----------+----------+----------+ 1920
     GAAGCGTTATCGCTGATTTATAACAAAGATCTGCTGCCGAACCCGCCAAAAACCTGGGAA
      E  A  L  S  L  I  Y  N  K  D  L  L  P  N  P  P  K  T  W  E

1921 ----------+----------+----------+----------+----------+----------+ 1980
     GAGATCCCGGCGCTGGATAAAGAACTGAAAGCGAAAGGTAAGACCGCGCTGATGTTCAAC
      E  I  P  A  L  D  K  E  L  K  A  K  G  K  T  A  L  M  F  N

1981 ----------+----------+----------+----------+----------+----------+ 2040
     CTGCAAGAACCGTACTTCACCTGGCCGCTGATTGCTGCTGACGGGGGCTATGCGTTCAAG
      L  Q  E  P  Y  F  T  W  P  L  I  A  A  D  G  G  Y  A  F  K

2041 ----------+----------+----------+----------+----------+----------+ 2100
     TATGAAAACGGCAAGTACGACATTAAAGACGTGGGCGTGGATAACGCTGGCGCGAAAGCG
      Y  E  N  G  K  Y  D  I  K  D  V  G  V  D  N  A  G  A  K  A
```

FIG. 2C-2
S146T Mutant

```
2101 ----------+----------+----------+----------+----------+----------+ 2160
     GGTCTGACCTTCCTGGTTGACCTGATTAAAAACAAACACATGAATGCAGACACCGATTAC
     G  L  T  F  L  V  D  L  I  K  N  K  H  M  N  A  D  T  D  Y

2161 ----------+----------+----------+----------+----------+----------+ 2220
     TCCATCGCAGAAGCTGCCTTTAATAAAGGCGAAACAGCGATGACCATCAACGGCCCGTGG
     S  I  A  E  A  A  F  N  K  G  E  T  A  M  T  I  N  G  P  W

2221 ----------+----------+----------+----------+----------+----------+ 2280
     GCATGGTCCAACATCGACACCAGCAAAGTGAATTATGGTGTAACGGTACTGCCGACCTTC
     A  W  S  N  I  D  T  S  K  V  N  Y  G  V  T  V  L  P  T  F

2281 ----------+----------+----------+----------+----------+----------+ 2340
     AAGGGTCAACCATCCAAACCGTTCGTTGGCGTGCTGAGCGCAGGTATTAACGCCGCCAGT
     K  G  Q  P  S  K  P  F  V  G  V  L  S  A  G  I  N  A  A  S

2341 ----------+----------+----------+----------+----------+----------+ 2400
     CCGAACAAAGAGCTGGCAAAAGAGTTCCTCGAAAACTATCTGCTGACTGATGAAGGTCTG
     P  N  K  E  L  A  K  E  F  L  E  N  Y  L  L  T  D  E  G  L

2401 ----------+----------+----------+----------+----------+----------+ 2460
     GAAGCGGTTAATAAAGACAAACCGCTGGGTGCCGTAGCGCTGAAGTCTTACGAGGAAGAG
     E  A  V  N  K  D  K  P  L  G  A  V  A  L  K  S  Y  E  E  E

2461 ----------+----------+----------+----------+----------+----------+ 2520
     TTGGCGAAAGATCCACGTATTGCCGCCACTATGGAAAACGCCCAGAAAGGTGAAATCATG
     L  A  K  D  P  R  I  A  A  T  M  E  N  A  Q  K  G  E  I  M

2521 ----------+----------+----------+----------+----------+----------+ 2580
     CCGAACATCCCGCAGATGTCCGCTTTCTGGTATGCCGTGCGTACTGCGGTGATCAACGCC
     P  N  I  P  Q  M  S  A  F  W  Y  A  V  R  T  A  V  I  N  A

2581 ----------+----------+----------+----------+----------+----------+ 2640
     GCCAGCGGTCGTCAGACTGTCGATGAAGCCCTGAAAGACGCGCAGACTAATTCGAGCTCG
     A  S  G  R  Q  T  V  D  E  A  L  K  D  A  Q  T  N  S  S  S

2641 ----------+----------+----------+----------+--------- 2688
     AACAACAACAACAATAACAATAACAACAACCTCGGGATCGAGGGAAGG
     N  N  N  N  N  N  N  N  N  N  L  G  I  E  G  R
```

FIG. 2D-1
MBP F68L (SEQ ID NOS:7 and 8)

```
1501 ----------+----------+----------+----------+----------+----------+ 1560
     GCACTTCACCAACAAGGACCATAGCATATGAAAATCGAAGAAGGTAAACTGGTAATCTGG
                                   M  K  I  E  E  G  K  L  V  I  W

1561 ----------+----------+----------+----------+----------+----------+ 1620
     ATTAACGGCGATAAAGGCTATAACGGTCTCGCTGAAGTCGGTAAGAAATTCGAGAAAGAT
     I  N  G  D  K  G  Y  N  G  L  A  E  V  G  K  K  F  E  K  D

1621 ----------+----------+----------+----------+----------+----------+ 1680
     ACCGGAATTAAAGTCACCGTTGAGCATCCGGATAAACTGGAAGAGAAATTCCCACAGGTT
     T  G  I  K  V  T  V  E  H  P  D  K  L  E  E  K  F  P  Q

1681 ----------+----------+----------+----------+----------+----------+ 1740
     GCGGCAACTGGCGATGGCCCTGACATTATCTTCTGGGCACACGACCGCCTTGGTGGCTAC
     A  A  T  G  D  G  P  D  I  I  F  W  A  H  D  R  L  G  G  Y

1741 ----------+----------+----------+----------+----------+----------+ 1800
     GCTCAATCTGGCCTGTTGGCTGAAATCACCCCGGACAAAGCGTTCCAGGACAAGCTGTAT
     A  Q  S  G  L  L  A  E  I  T  P  D  K  A  F  Q  D  K  L

1801 ----------+----------+----------+----------+----------+----------+ 1860
     CCGTTTACCTGGGATGCCGTACGTTACAACGGCAAGCTGATTGCTTACCCGATCGCTGTT
     P  F  T  W  D  A  V  R  Y  N  G  K  L  I  A  Y  P  I  A  V

1861 ----------+----------+----------+----------+----------+----------+ 1920
     GAAGCGTTATCGCTGATTTATAACAAAGATCTGCTGCCGAACCCGCCAAAAACCTGGGAA
     E  A  L  S  L  I  Y  N  K  D  L  L  P  N  P  P  K  T  W  E

1921 ----------+----------+----------+----------+----------+----------+ 1980
     GAGATCCCGGCGCTGGATAAAGAACTGAAAGCGAAAGGTAAGAGCGCGCTGATGTTCAAC
     E  I  P  A  L  D  K  E  L  K  A  K  G  K  S  A  L  M  F

1981 ----------+----------+----------+----------+----------+----------+ 2040
     CTGCAAGAACCGTACTTCACCTGGCCGCTGATTGCTGCTGACGGGGGTTATGCGTTCAAG
     L  Q  E  P  Y  F  T  W  P  L  I  A  A  D  G  G  Y  A  F  K

2041 ----------+----------+----------+----------+----------+----------+ 2100
     TATGAAAACGGCAAGTACGACATTAAAGACGTGGGCGTGGATAACGCTGGCGCGAAAGCG
     Y  E  N  G  K  Y  D  I  K  D  V  G  V  D  N  A  G  A  K  A
```

FIG. 2D-2
MBP F68L

```
2101 ----------+----------+----------+----------+----------+----------+ 2160
     GGTCTGACCTTCCTGGTTGACCTGATTAAAAACAAACACATGAATGCAGACACCGATTAC
     G  L  T  F  L  V  D  L  I  K  N  K  H  M  N  A  D  T  D  Y

2161 ----------+----------+----------+----------+----------+----------+ 2220
     TCCATCGCAGAAGCTGCCTTTAATAAAGGCGAAACAGCGATGACCATCAACGGCCCGTGG
      S  I  A  E  A  A  F  N  K  G  E  T  A  M  T  I  N  G  P  W

2221 ----------+----------+----------+----------+----------+----------+ 2280
     GCATGGTCCAACATCGACACCAGCAAAGTGAATTATGGTGTAACGGTACTGCCGACCTTC
     A  W  S  N  I  D  T  S  K  V  N  Y  G  V  T  V  L  P  T  F

2281 ----------+----------+----------+----------+----------+----------+ 2340
     AAGGGTCAACCATCCAAACCGTTCGTTGGCGTGCTGAGCGCAGGTATTAACGCCGCCAGT
     K  G  Q  P  S  K  P  F  V  G  V  L  S  A  G  I  N  A  A  S

2341 ----------+----------+----------+----------+----------+----------+ 2400
     CCGAACAAAGAGCTGGCAAAAGAGTTCCTCGAAAACTATCTGCTGACTGATGAAGGTCTG
     P  N  K  E  L  A  K  E  F  L  E  N  Y  L  L  T  D  E  G  L

2401 ----------+----------+----------+----------+----------+----------+ 2460
     GAAGCGGTTAATAAAGACAAACCGCTGGGTGCCGTAGCGCTGAAGTCTTACGAGGAAGAG
     E  A  V  N  K  D  K  P  L  G  A  V  A  L  K  S  Y  E  E  E

2461 ----------+----------+----------+----------+----------+----------+ 2520
     TTGGCGAAAGATCCACGTATTGCCGCCACTATGGAAAACGCCCAGAAAGGTGAAATCATG
     L  A  K  D  P  R  I  A  A  T  M  E  N  A  Q  K  G  E  I  M

2521 ----------+----------+----------+----------+----------+----------+ 2580
     CCGAACATCCCGCAGATGTCCGCTTTCTGGTATGCCGTGCGTACTGCGGTGATCAACGCC
     P  N  I  P  Q  M  S  A  F  W  Y  A  V  R  T  A  V  I  N  A

2581 ----------+----------+----------+----------+----------+----------+ 2640
     GCCAGCGGTCGTCAGACTGTCGATGAAGCCCTGAAAGACGCGCAGACTAATTCGAGCTCG
     A  S  G  R  Q  T  V  D  E  A  L  K  D  A  Q  T  N  S  S  S

2641 ----------+----------+----------+----------+-------- 2688
     AACAACAACAACAATAACAATAACAACAACCTCGGGATCGAGGGAAGG
     N  N  N  N  N  N  N  N  N  N  L  G  I  E  G  R
```

FIG. 2E-1
MBP I318V (SEQ ID NOS:9 and 10)

```
1501 ----------+----------+----------+----------+----------+----------+ 1560
     GCACTTCACCAACAAGGACCATAGCATATGAAAATCGAAGAAGGTAAACTGGTAATCTGG
                                  M  K  I  E  E  G  K  L  V  I  W

1561 ----------+----------+----------+----------+----------+----------+ 1620
     ATTAACGGCGATAAAGGCTATAACGGTCTCGCTGAAGTCGGTAAGAAATTCGAGAAAGAT
     I  N  G  D  K  G  Y  N  G  L  A  E  V  G  K  K  F  E  K  D

1621 ----------+----------+----------+----------+----------+----------+ 1680
     ACCGGAATTAAAGTCACCGTTGAGCATCCGGATAAACTGGAAGAGAAATTCCCACAGGTT
     T  G  I  K  V  T  V  E  H  P  D  K  L  E  E  K  F  P  Q  V

1681 ----------+----------+----------+----------+----------+----------+ 1740
     GCGGCAACTGGCGATGGCCCTGACATTATCTTCTGGGCACACGACCGCTTTGGTGGCTAC
     A  A  T  G  D  G  P  D  I  I  F  W  A  H  D  R  F  G  G  Y

1741 ----------+----------+----------+----------+----------+----------+ 1800
     GCTCAATCTGGCCTGTTGGCTGAAATCACCCCGGACAAAGCGTTCCAGGACAAGCTGTAT
     A  Q  S  G  L  L  A  E  I  T  P  D  K  A  F  Q  D  K  L  Y

1801 ----------+----------+----------+----------+----------+----------+ 1860
     CCGTTTACCTGGGATGCCGTACGTTACAACGGCAAGCTGATTGCTTACCCGATCGCTGTT
     P  F  T  W  D  A  V  R  Y  N  G  K  L  I  A  Y  P  I  A  V

1861 ----------+----------+----------+----------+----------+----------+ 1920
     GAAGCGTTATCGCTGATTTATAACAAAGATCTGCTGCCGAACCCGCCAAAAACCTGGGAA
     E  A  L  S  L  I  Y  N  K  D  L  L  P  N  P  P  K  T  W  E

1921 ----------+----------+----------+----------+----------+----------+ 1980
     GAGATCCCGGCGCTGGATAAAGAACTGAAAGCGAAAGGTAAGAGCGCGCTGATGTTCAAC
     E  I  P  A  L  D  K  E  L  K  A  K  G  K  S  A  L  M  F  N

1981 ----------+----------+----------+----------+----------+----------+ 2040
     CTGCAAGAACCGTACTTCACCTGGCCGCTGATTGCTGCTGACGGGGGTTATGCGTTCAAG
     L  Q  E  P  Y  F  T  W  P  L  I  A  A  D  G  G  Y  A  F  K

2041 ----------+----------+----------+----------+----------+----------+ 2100
     TATGAAAACGGCAAGTACGACATTAAAGACGTGGGCGTGGATAACGCTGGCGCGAAAGCG
     Y  E  N  G  K  Y  D  I  K  D  V  G  V  D  N  A  G  A  K  A
```

FIG. 2E-2
MBP I318V

```
2101 ----------+---------+----------+----------+----------+---------+ 2160
     GGTCTGACCTTCCTGGTTGACCTGATTAAAAACAAACACATGAATGCAGACACCGATTAC
      G  L  T  F  L  V  D  L  I  K  N  K  H  M  N  A  D  T  D  Y

2161 ----------+---------+----------+----------+----------+---------+ 2220
     TCCATCGCAGAAGCTGCCTTTAATAAAGGCGAAACAGCGATGACCATCAACGGCCCGTGG
      S  I  A  E  A  A  F  N  K  G  E  T  A  M  T  I  N  G  P  W

2221 ----------+---------+----------+----------+----------+---------+ 2280
     GCATGGTCCAACATCGACACCAGCAAAGTGAATTATGGTGTAACGGTACTGCCGACCTTC
      A  W  S  N  I  D  T  S  K  V  N  Y  G  V  T  V  L  P  T  F

2281 ----------+---------+----------+----------+----------+---------+ 2340
     AAGGGTCAACCATCCAAACCGTTCGTTGGCGTGCTGAGCGCAGGTATTAACGCCGCCAGT
      K  G  Q  P  S  K  P  F  V  G  V  L  S  A  G  I  N  A  A  S

2341 ----------+---------+----------+----------+----------+---------+ 2400
     CCGAACAAAGAGCTGGCAAAAGAGTTCCTCGAAAACTATCTGCTGACTGATGAAGGTCTG
      P  N  K  E  L  A  K  E  F  L  E  N  Y  L  L  T  D  E  G  L

2401 ----------+---------+----------+----------+----------+---------+ 2460
     GAAGCGGTTAATAAAGACAAACCGCTGGGTGCCGTAGCGCTGAAGTCTTACGAGGAAGAG
      E  A  V  N  K  D  K  P  L  G  A  V  A  L  K  S  Y  E  E  E

2461 ----------+---------+----------+----------+----------+---------+ 2520
     TTGGCGAAAGATCCACGTGTTGCCGCCACTATGGAAAACGCCCAGAAAGGTGAAATCATG
      L  A  K  D  P  R  V  A  A  T  M  E  N  A  Q  K  G  E  I  M

2521 ----------+---------+----------+----------+----------+---------+ 2580
     CCGAACATCCCGCAGATGTCCGCTTTCTGGTATGCCGTGCGTACTGCGGTGATCAACGCC
      P  N  I  P  Q  M  S  A  F  W  Y  A  V  R  T  A  V  I  N  A

2581 ----------+---------+----------+----------+----------+---------+ 2640
     GCCAGCGGTCGTCAGACTGTCGATGAAGCCCTGAAAGACGCGCAGACTAATTCGAGCTCG
      A  S  G  R  Q  T  V  D  E  A  L  K  D  A  Q  T  N  S  S  S

2641 ----------+---------+----------+----------+--------- 2688
     AACAACAACAACAATAACAATAACAACAACCTCGGGATCGAGGGAAGG
      N  N  N  N  N  N  N  N  N  N  L  G  I  E  G  R
```

FIG. 2F-1
MBP Q326R (SEQ ID NOS:11 and 12)

```
1501 ----------+----------+----------+----------+----------+----------+ 1560
     GCACTTCACCAACAAGGACCATAGCATATGAAAATCGAAGAAGGTAAACTGGTAATCTGG
                              M  K  I  E  E  G  K  L  V  I  W
1561 ----------+----------+----------+----------+----------+----------+ 1620
     ATTAACGGCGATAAAGGCTATAACGGTCTCGCTGAAGTCGGTAAGAAATTCGAGAAAGAT
      I  N  G  D  K  G  Y  N  G  L  A  E  V  G  K  K  F  E  K  D
1621 ----------+----------+----------+----------+----------+----------+ 1680
     ACCGGAATTAAAGTCACCGTTGAGCATCCGGATAAACTGGAAGAGAAATTCCCACAGGTT
      T  G  I  K  V  T  V  E  H  P  D  K  L  E  E  K  F  P  Q  V
1681 ----------+----------+----------+----------+----------+----------+ 1740
     GCGGCAACTGGCGATGGCCCTGACATTATCTTCTGGGCACACGACCGCTTTGGTGGCTAC
      A  A  T  G  D  G  P  D  I  I  F  W  A  H  D  R  F  G  G  Y
1741 ----------+----------+----------+----------+----------+----------+ 1800
     GCTCAATCTGGCCTGTTGGCTGAAATCACCCCGGACAAAGCGTTCCAGGACAAGCTGTAT
      A  Q  S  G  L  L  A  E  I  T  P  D  K  A  F  Q  D  K  L  Y
1801 ----------+----------+----------+----------+----------+----------+ 1860
     CCGTTTACCTGGGATGCCGTACGTTACAACGGCAAGCTGATTGCTTACCCGATCGCTGTT
      P  F  T  W  D  A  V  R  Y  N  G  K  L  I  A  Y  P  I  A  V
1861 ----------+----------+----------+----------+----------+----------+ 1920
     GAAGCGTTATCGCTGATTTATAACAAAGATCTGCTGCCCGAACCCGCCAAAAACCTGGGAA
      E  A  L  S  L  I  Y  N  K  D  L  L  P  N  P  P  K  T  W
1921 ----------+----------+----------+----------+----------+----------+ 1980
     GAGATCCCGGCGCTGGATAAAGAACTGAAAGCGAAAGGTAAGAGCGCGCTGATGTTCAAC
      E  I  P  A  L  D  K  E  L  K  A  K  G  K  S  A  L  M  F
1981 ----------+----------+----------+----------+----------+----------+ 2040
     CTGCAAGAACCGTACTTCACCTGGCCGCTGATTGCTGCTGACGGGGGTTATGCGTTCAAG
      L  Q  E  P  Y  F  T  W  P  L  I  A  A  D  G  G  Y  A  F
2041 ----------+----------+----------+----------+----------+----------+ 2100
     TATGAAAACGGCAAGTACGACATTAAAGACGTGGGCGTGGATAACGCTGGCGCGAAAGCG
      Y  E  N  G  K  Y  D  I  K  D  V  G  V  D  N  A  G  A  K  A
```

FIG. 2F-2
MBP Q326R

```
2101 ----------+----------+----------+----------+----------+----------+ 2160
     GGTCTGACCTTCCTGGTTGACCTGATTAAAAACAAACACATGAATGCAGACACCGATTAC
      G  L  T  F  L  V  D  L  I  K  N  K  H  M  N  A  D  T  D  Y

2161 ----------+----------+----------+----------+----------+----------+ 2220
     TCCATCGCAGAAGCTGCCTTTAATAAAGGCGAAACAGCGATGACCATCAACGGCCCGTGG
      S  I  A  E  A  A  F  N  K  G  E  T  A  M  T  I  N  G  P  W

2221 ----------+----------+----------+----------+----------+----------+ 2280
     GCATGGTCCAACATCGACACCAGCAAAGTGAATTATGGTGTAACGGTACTGCCGACCTTC
      A  W  S  N  I  D  T  S  K  V  N  Y  G  V  T  V  L  P  T  F

2281 ----------+----------+----------+----------+----------+----------+ 2340
     AAGGGTCAACCATCCAAACCGTTCGTTGGCGTGCTGAGCGCAGGTATTAACGCCGCCAGT
      K  G  Q  P  S  K  P  F  V  G  V  L  S  A  G  I  N  A  A  S

2341 ----------+----------+----------+----------+----------+----------+ 2400
     CCGAACAAAGAGCTGGCAAAAGAGTTCCTCGAAAACTATCTGCTGACTGATGAAGGTCTG
      P  N  K  E  L  A  K  E  F  L  E  N  Y  L  L  T  D  E  G  L

2401 ----------+----------+----------+----------+----------+----------+ 2460
     GAAGCGGTTAATAAAGACAAACCGCTGGGTGCCGTAGCGCTGAAGTCTTACGAGGAAGAG
      E  A  V  N  K  D  K  P  L  G  A  V  A  L  K  S  Y  E  E  E

2461 ----------+----------+----------+----------+----------+----------+ 2520
     TTGGCGAAAGATCCACGTATTGCCGCCACTATGGAAAACGCCCGGAAAGGTGAAATCATG
      L  A  K  D  P  R  I  A  A  T  M  E  N  A  R  K  G  E  I  M

2521 ----------+----------+----------+----------+----------+----------+ 2580
     CCGAACATCCCGCAGATGTCCGCTTTCTGGTATGCCGTGCGTACTGCGGTGATCAACGCC
      P  N  I  P  Q  M  S  A  F  W  Y  A  V  R  T  A  V  I  N

2581 ----------+----------+----------+----------+----------+----------+ 2640
     GCCAGCGGTCGTCAGACTGTCGATGAAGCCCTGAAAGACGCGCAGACTAATTCGAGCTCG
      A  S  G  R  Q  T  V  D  E  A  L  K  D  A  Q  T  N  S  S  S

2641 ----------+----------+----------+----------+--------- 2688
     AACAACAACAACAATAACAATAACAACAACCTCGGGATCGAGGGAAGG
      N  N  N  N  N  N  N  N  N  N  L  G  I  E  G  R
```

FIG. 2G-1
MBP V344M (SEQ ID NOS:13 and 14)

```
1501 ----------+----------+----------+----------+----------+----------+ 1560
     GCACTTCACCAACAAGGACCATAGCATATGAAAATCGAAGAAGGTAAACTGGTAATCTGG
                                 M  K  I  E  E  G  K  L  V  I  W
1561 ----------+----------+----------+----------+----------+----------+ 1620
     ATTAACGGCGATAAAGGCTATAACGGTCTCGCTGAAGTCGGTAAGAAATTCGAGAAAGAT
      I  N  G  D  K  G  Y  N  G  L  A  E  V  G  K  K  F  E  K  D
1621 ----------+----------+----------+----------+----------+----------+ 1680
     ACCGGAATTAAAGTCACCGTTGAGCATCCGGATAAACTGGAAGAGAAATTCCCACAGGTT
      T  G  I  K  V  T  V  E  H  P  D  K  L  E  E  K  F  P  Q  V
1681 ----------+----------+----------+----------+----------+----------+ 1740
     GCGGCAACTGGCGATGGCCCTGACATTATCTTCTGGGCACACGACCGCTTTGGTGGCTAC
      A  A  T  G  D  G  P  D  I  I  F  W  A  H  D  R  F  G  G  Y
1741 ----------+----------+----------+----------+----------+----------+ 1800
     GCTCAATCTGGCCTGTTGGCTGAAATCACCCCGGACAAAGCGTTCCAGGACAAGCTGTAT
      A  Q  S  G  L  L  A  E  I  T  P  D  K  A  F  Q  D  K  L  Y
1801 ----------+----------+----------+----------+----------+----------+ 1860
     CCGTTTACCTGGGATGCCGTACGTTACAACGGCAAGCTGATTGCTTACCCGATCGCTGTT
      P  F  T  W  D  A  V  R  Y  N  G  K  L  I  A  Y  P  I  A  V
1861 ----------+----------+----------+----------+----------+----------+ 1920
     GAAGCGTTATCGCTGATTTATAACAAAGATCTGCTGCCGAACCCGCCAAAAACCTGGGAA
      E  A  L  S  L  I  Y  N  K  D  L  L  P  N  P  P  K  T  W  E
1921 ----------+----------+----------+----------+----------+----------+ 1980
     GAGATCCCGGCGCTGGATAAAGAACTGAAAGCGAAAGGTAAGAGCGCGCTGATGTTCAAC
      E  I  P  A  L  D  K  E  L  K  A  K  G  K  S  A  L  M  F  N
1981 ----------+----------+----------+----------+----------+----------+ 2040
     CTGCAAGAACCGTACTTCACCTGGCCGCTGATTGCTGCTGACGGGGGTTATGCGTTCAAG
      L  Q  E  P  Y  F  T  W  P  L  I  A  A  D  G  G  Y  A  F  K
2041 ----------+----------+----------+----------+----------+----------+ 2100
     TATGAAAACGGCAAGTACGACATTAAAGACGTGGGCGTGGATAACGCTGGCGCGAAAGCG
      Y  E  N  G  K  Y  D  I  K  D  V  G  V  D  N  A  G  A  K  A
```

FIG. 2G-2
MBP V344M

```
2101 ----------+----------+----------+----------+----------+----------+ 2160
     GGTCTGACCTTCCTGGTTGACCTGATTAAAAACAAACACATGAATGCAGACACCGATTAC
      G  L  T  F  L  V  D  L  I  K  N  K  H  M  N  A  D  T  D  Y

2161 ----------+----------+----------+----------+----------+----------+ 2220
     TCCATCGCAGAAGCTGCCTTTAATAAAGGCGAAACAGCGATGACCATCAACGGCCCGTGG
      S  I  A  E  A  A  F  N  K  G  E  T  A  M  T  I  N  G  P  W

2221 ----------+----------+----------+----------+----------+----------+ 2280
     GCATGGTCCAACATCGACACCAGCAAAGTGAATTATGGTGTAACGGTACTGCCGACCTTC
      A  W  S  N  I  D  T  S  K  V  N  Y  G  V  T  V  L  P  T  F

2281 ----------+----------+----------+----------+----------+----------+ 2340
     AAGGGTCAACCATCCAAACCGTTCGTTGGCGTGCTGAGCGCAGGTATTAACGCCGCCAGT
      K  G  Q  P  S  K  P  F  V  G  V  L  S  A  G  I  N  A  A  S

2341 ----------+----------+----------+----------+----------+----------+ 2400
     CCGAACAAAGAGCTGGCAAAAGAGTTCCTCGAAAACTATCTGCTGACTGATGAAGGTCTG
      P  N  K  E  L  A  K  E  F  L  E  N  Y  L  L  T  D  E  G  L

2401 ----------+----------+----------+----------+----------+----------+ 2460
     GAAGCGGTTAATAAAGACAAACCGCTGGGTGCCGTAGCGCTGAAGTCTTACGAGGAAGAG
      E  A  V  N  K  D  K  P  L  G  A  V  A  L  K  S  Y  E  E  E

2461 ----------+----------+----------+----------+----------+----------+ 2520
     TTGGCGAAAGATCCACGTATTGCCGCCACTATGGAAAACGCCCAGAAAGGTGAAATCATG
      L  A  K  D  P  R  I  A  A  T  M  E  N  A  Q  K  G  E  I  M

2521 ----------+----------+----------+----------+----------+----------+ 2580
     CCGAACATCCCGCAGATGTCCGCTTTCTGGTATGCCATGCGTACTGCGGTGATCAACGCC
      P  N  I  P  Q  M  S  A  F  W  Y  A  M  R  T  A  V  I  N  A

2581 ----------+----------+----------+----------+----------+----------+ 2640
     GCCAGCGGTCGTCAGACTGTCGATGAAGCCCTGAAAGACGCGCAGACTAATTCGAGCTCG
      A  S  G  R  Q  T  V  D  E  A  L  K  D  A  Q  T  N  S  S  S

2641 ----------+----------+----------+----------+--------- 2688
     AACAACAACAACAATAACAATAACAACAACCTCGGGATCGAGGGAAGG
      N  N  N  N  N  N  N  N  N  N  L  G  I  E  G  R
```

FIG. 2H-1
MBP T/I (SEQ ID NOS:15 and 16)

```
1501 ----------+----------+----------+----------+----------+----------+ 1560
     GCACTTCACCAACAAGGACCATAGCATATGAAAATCGAAGAAGGTAAACTGGTAATCTGG
                                  M  K  I  E  E  G  K  L  V  I  W

1561 ----------+----------+----------+----------+----------+----------+ 1620
     ATTAACGGCGATAAAGGCTATAACGGTCTCGCTGAAGTCGGTAAGAAATTCGAGAAAGAT
      I  N  G  D  K  G  Y  N  G  L  A  E  V  G  K  K  F  E  K  D

1621 ----------+----------+----------+----------+----------+----------+ 1680
     ACCGGAATTAAAGTCACCGTTGAGCATCCGGATAAACTGGAAGAGAAATTCCCACAGGTT
      T  G  I  K  V  T  V  E  H  P  D  K  L  E  E  K  F  P  Q  V

1681 ----------+----------+----------+----------+----------+----------+ 1740
     GCGGCAACTGGCGATGGCCCTGACATTATCTTCTGGGCACACGACCGCTTTGGTGGCTAC
      A  A  T  G  D  G  P  D  I  I  F  W  A  H  D  R  F  G  G  Y

1741 ----------+----------+----------+----------+----------+----------+ 1800
     GCTCAATCTGGCCTGTTGGCTGAAATCACCCCGGACAAAGCGTTCCAGGACAAGCTGTAT
      A  Q  S  G  L  L  A  E  I  T  P  D  K  A  F  Q  D  K  L  Y

1801 ----------+----------+----------+----------+----------+----------+ 1860
     CCGTTTACCTGGGATGCCGTACGTTACAACGGCAAGCTGATTGCTTACCCGATCGCTGTT
      P  F  T  W  D  A  V  R  Y  N  G  K  L  I  A  Y  P  I  A  V

1861 ----------+----------+----------+----------+----------+----------+ 1920
     GAAGCGTTATCGCTGATTTATAACAAAGATCTGCTGCCGAACCCGCCAAAAACCTGGGAA
      E  A  L  S  L  I  Y  N  K  D  L  L  P  N  P  P  K  T  W  E

1921 ----------+----------+----------+----------+----------+----------+ 1980
     GAGATCCCGGCGCTGGATAAAGAACTGAAAGCGAAAGGTAAGAGCGCGCTGATGTTCAAC
      E  I  P  A  L  D  K  E  L  K  A  K  G  K  S  A  L  M  F  N

1981 ----------+----------+----------+----------+----------+----------+ 2040
     CTGCAAGAACCGTACTTCACCTGGCCGCTGATTGCTGCTGACGGGGGTTATGCGTTCAAG
      L  Q  E  P  Y  F  T  W  P  L  I  A  A  D  G  G  Y  A  F  K

2041 ----------+----------+----------+----------+----------+----------+ 2100
     TATGAAAACGGCAAGTACGACATTAAAGACGTGGGCGTGGATAACGCTGGCGCGAAAGCG
      Y  E  N  G  K  Y  D  I  K  D  V  G  V  D  N  A  G  A  K  A
```

FIG. 2H-2
MBP T/I

```
2101 ---------+---------+---------+---------+---------+---------+ 2160
     GGTCTGACCTTCCTGGTTGACCTGATTAAAAACAAACACATGAATGCAGACACCGATTAC
      G  L  T  F  L  V  D  L  I  K  N  K  H  M  N  A  D  T  D  Y

2161 ---------+---------+---------+---------+---------+---------+ 2220
     TCCATCGCAGAAGCTGCCTTTAATAAAGGCGAAACAGCGATGACCATCAACGGCCCGTGG
      S  I  A  E  A  A  F  N  K  G  E  T  A  M  T  I  N  G  P  W

2221 ---------+---------+---------+---------+---------+---------+ 2280
     GCATGGTCCAACATCGACACCAGCAAAGTGAATTATGGTGTAACGGTACTGCCGACCTTC
      A  W  S  N  I  D  T  S  K  V  N  Y  G  V  T  V  L  P  T  F

2281 ---------+---------+---------+---------+---------+---------+ 2340
     AAGGGTCAACCATCCAAACCGTTCGTTGGCGTGCTGAGCGCAGGTATTAACGCCGCCAGT
      K  G  Q  P  S  K  P  F  V  G  V  L  S  A  G  I  N  A  A  S

2341 ---------+---------+---------+---------+---------+---------+ 2400
     CCGAACAAAGAGCTGGCAAAAGAGTTCCTCGAAAACTATCTGCTGACTGATGAAGGTCTG
      P  N  K  E  L  A  K  E  F  L  E  N  Y  L  L  T  D  E  G  L

2401 ---------+---------+---------+---------+---------+---------+ 2460
     GAAGCGGTTAATAAAGACAAACCGCTGGGTGCCGTAGCGCTGAAGTCTTACGAGGAAGAG
      E  A  V  N  K  D  K  P  L  G  A  V  A  L  K  S  Y  E  E  E

2461 ---------+---------+---------+---------+---------+---------+ 2520
     TTGGCGAAAGATCCACGTATTGCCGCCACTATGGAAAACGCCCAGAAAGGTGAAATCATG
      L  A  K  D  P  R  I  A  A  T  M  E  N  A  Q  K  G  E  I  M

2521 ---------+---------+---------+---------+---------+---------+ 2580
     CCGAACATCCCGCAGATGTCCGCTTTCTGGTATGCCGTGCGTACTGCGGTGATCAACGCC
      P  N  I  P  Q  M  S  A  F  W  Y  A  V  R  T  A  V  I  N  A

2581 ---------+---------+---------+---------+---------+---------+ 2640
     GCCAGCGGTCGTCAGACTGTCGATGAAGCCCTGAAAGACGCGCAGACTAATTCGAGCTCA
      A  S  G  R  Q  T  V  D  E  A  L  K  D  A  Q  T  N  S  S  S

2641 ---------+---------+---------+---------+--------- 2688
     ACTACTACCACCATAACTATAACCACTACCCTCGGGATCGAGGGAAGG
      T  T  T  T  I  T  I  T  T  T  L  G  I  E  G  R
```

FIG. 3-1
pIH1684 (SEQ ID NO:17)

```
   1 CCGACACCAT CGAATGGTGC AAAACCTTTC GCGGTATGGC ATGATAGCGC CCGGAAGAGA
  61 GTCAATTCAG GGTGGTGAAT GTGAAACCAG TAACGTTATA CGATGTCGCA GAGTATGCCG
 121 GTGTCTCTTA TCAGACCGTT TCCCGCGTGG TGAACCAGGC CAGCCACGTT TCTGCGAAAA
 181 CGCGGGAAAA AGTGGAAGCG GCGATGGCGG AGCTGAATTA CATTCCCAAC CGCGTGGCAC
 241 AACAACTGGC GGGCAAACAG TCGTTGCTGA TTGGCGTTGC CACCTCCAGT CTGGCCCTGC
 301 ACGCGCCGTC GCAAATTGTC GCGGCGATTA AATCTCGCGC CGATCAACTG GGTGCCAGCG
 361 TGGTGGTGTC GATGGTAGAA CGAAGCGGCG TCGAAGCCTG TAAAGCGGCG GTGCACAATC
 421 TTCTCGCGCA ACGCGTCAGT GGGCTGATCA TTAACTATCC GCTGGATGAC CAGGATGCCA
 481 TTGCTGTGGA AGCTGCCTGC ACTAATGTTC CGGCGTTATT TCTTGATGTC TCTGACCAGA
 541 CACCCATCAA CAGTATTATT TTCTCCCATG AAGACGGTAC GCGACTGGGC GTGGAGCATC
 601 TGGTCGCATT GGGTCACCAG CAAATCGCGC TGTTAGCGGG CCCATTAAGT TCTGTCTCGG
 661 CGCGTCTGCG TCTGGCTGGC TGGCATAAAT ATCTCACTCG CAATCAAATT CAGCCGATAG
 721 CGGAACGGGA AGGCGACTGG AGTGCCATGT CCGGTTTTCA ACAAACCATG CAAATGCTGA
 781 ATGAGGGCAT CGTTCCCACT GCGATGCTGG TTGCCAACGA TCAGATGGCG CTGGGCGCAA
 841 TGCGCGCCAT TACCGAGTCC GGGCTGCGCG TTGGTGCGGA CATCTCGGTA GTGGGATACG
 901 ACGATACCGA AGACAGCTCA TGTTATATCC CGCCGTTAAC CACCATCAAA CAGGATTTTC
 961 GCCTGCTGGG GCAAACCAGC GTGGACCGCT TGCTGCAACT CTCTCAGGGC CAGGCGGTGA
1021 AGGGCAATCA GCTGTTGCCC GTCTCACTGG TGAAAAGAAA AACCACCCTG GCGCCCAATA
1081 CGCAAACCGC CTCTCCCCGC GCGTTGGCCG ATTCATTAAT GCAGCTGGCA CGACAGGTTT
1141 CCCGACTGGA AAGCGGGCAG TGAGCGCAAC GCAATTAATG TAAGTTAGCT CACTCATTAG
1201 GCACAATTCT CATGTTTGAC AGCTTATCAT CGACTGCACG GTGCACCAAT GCTTCTGGCG
1261 TCAGGCAGCC ATCGGAAGCT GTGGTATGGC TGTGCAGGTC GTAAATCACT GCATAATTCG
1321 TGTCGCTCAA GGCGCACTCC CGTTCTGGAT AATGTTTTTT GCGCCGACAT CATAACGGTT
1381 CTGGCAAATA TTCTGAAATG AGCTGTTGAC AATTAATCAT CGGCTCGTAT AATGTGTGGA
1441 ATTGTGAGCG GATAACAATT TCACACAGGA AACAGCCAGT CCGTTTAGGT GTTTTCACGA
1501 GCAATTGACC AACAAGGACC ATAGATTATG AAAATCGAAG AAGGTAAACT GGTAATCTGG
1561 ATTAACGGCG ATAAAGGCTA TAACGGTCTC GCTGAAGTCG GTAAGAAATT CGAGAAAGAT
1621 ACCGGAATTA AAGTCACCGT TGAGCATCCG GATAAACTGG AAGAGAAATT CCCACAGGTT
1681 GCGGCAACTG GCGATGGCCC TGACATTATC TTCTGGGCAC ACGACCGCTT TGGTGGCTAC
1741 GCTCAATCTG GCCTGTTGGC TGAAATCACC CCGGACAAAG CGTTCCAGGA CAAGCTGTAT
1801 CCGTTTACCT GGGATGCCGT ACGTTACAAC GGCAAGCTGA TTGCTTACCC GATCGCTGTT
```

FIG. 3-2
pIH1684

```
1861 GAAGCGTTAT CGCTGATTTA TAACAAAGAT CTGCTGCCGA ACCCGCCAAA AACCTGGGAA
1921 GAGATCCCGG CGCTGGATAA AGAACTGAAA GCGAAAGGTA AGAGCGCGCT GATGTTCAAC
1981 CTGCAAGAAC CGTACTTCAC CTGGCCGCTG ATTGCTGCTG ACGGGGGTTA TGCGTTCAAG
2041 TATGAAAACG GCAAGTACGA CATTAAAGAC GTGGGCGTGG ATAACGCTGG CGCGAAAGCG
2101 GGTCTGACCT TCCTGGTTGA CCTGATTAAA AACAAACACA TGAATGCAGA CACCGATTAC
2161 TCCATCGCAG AAGCTGCCTT TAATAAAGGC GAAACAGCGA TGACCATCAA CGGCCCGTGG
2221 GCATGGTCCA ACATCGACAC CAGCAAAGTG AATTATGGTG TAACGGTACT GCCGACCTTC
2281 AAGGGTCAAC CATCCAAACC GTTCGTTGGC GTGCTGAGCG CAGGTATTAA CGCCGCCAGT
2341 CCGAACAAAG AGCTGGCAAA AGAGTTCCTC GAAAACTATC TGCTGACTGA TGAAGGTCTG
2401 GAAGCGGTTA ATAAAGACAA ACCGCTGGGT GCCGTAGCGC TGAAGTCTTA CGAGGAAGAG
2461 TTGGCGAAAG ATCCACGTAT TGCCGCCACT ATGGAAAACG CCCAGAAAGG TGAAATCATG
2521 CCGAACATCC CGCAGATGTC CGCTTTCTGG TATGCCGTGC GTACTGCGGT GATCAACGCC
2581 GCCAGCGGTC GTCAGACTGT CGATGAAGCC CTGAAAGACG CGCAGACTAA TTCGAGCTCG
2641 AACAACAACA ACAATAACAA TAACAACAAC CTCGGGATCG AGGGAAGGAT TTCACATATG
2701 TCCATGGGCG GCCGCGATAT CGTCGACGGA TCCGAATTCC CTGCAGGTAA TTAAATAAGC
2761 TTGGCACTGG CCGTCGTTTT ACAACGTCGT GACTGGGAAA ACCCTGGCGT TACCCAACTT
2821 AATCGCCTTG CAGCACATCC CCCTTTCGCC AGCTGGCGTA ATAGCGAAGA GGCCCGCACC
2881 GATCGCCCTT CCCAACAGTT GCGCAGCCTG AATGGCGAAT GGCAGCTTGG CTGTTTTGGC
2941 GGATGAGATA AGATTTTCAG CCTGATACAG ATTAAATCAG AACGCAGAAG CGGTCTGATA
3001 AAACAGAATT TGCCTGGCGG CAGTAGCGCG GTGGTCCCAC CTGACCCCAT GCCGAACTCA
3061 GAAGTGAAAC GCCGTAGCGC CGATGGTAGT GTGGGGTCTC CCCATGCGAG AGTAGGGAAC
3121 TGCCAGGCAT CAAATAAAAC GAAAGGCTCA GTCGAAAGAC TGGGCCTTTC GTTTTATCTG
3181 TTGTTTGTCG GTGAACGCTC TCCTGAGTAG GACAAATCCG CCGGGAGCGG ATTTGAACGT
3241 TGCGAAGCAA CGGCCCGGAG GGTGGCGGGC AGGACGCCCG CCATAAACTG CCAGGCATCA
3301 AATTAAGCAG AAGGCCATCC TGACGGATGG CCTTTTTGCG TTTCTACAAA CTCTTTTTGT
3361 TTATTTTTCT AAATACATTC AAATATGTAT CCGCTCATGA GACAATAACC CTGATAAATG
3421 CTTCAATAAT ATTGAAAAAG GAAGAGTATG AGTATTCAAC ATTTCCGTGT CGCCCTTATT
3481 CCCTTTTTTG CGGCATTTTG CCTTCCTGTT TTTGCTCACC CAGAAACGCT GGTGAAAGTA
3541 AAAGATGCTG AAGATCAGTT GGGTGCACGA GTGGGTTACA TCGAACTGGA TCTCAACAGC
3601 GGTAAGATCC TTGAGAGTTT TCGCCCCGAA GAACGTTCTC CAATGATGAG CACTTTTAAA
3661 GTTCTGCTAT GTGGCGCGGT ATTATCCCGT GTTGACGCCG GGCAAGAGCA ACTCGGTCGC
```

FIG. 3-3
pIH1684

```
3721 CGCATACACT ATTCTCAGAA TGACTTGGTT GAGTACTCAC CAGTCACAGA AAAGCATCTT
3781 ACGGATGGCA TGACAGTAAG AGAATTATGC AGTGCTGCCA TAACCATGAG TGATAACACT
3841 GCGGCCAACT TACTTCTGAC AACGATCGGA GGACCGAAGG AGCTAACCGC TTTTTTGCAC
3901 AACATGGGGG ATCATGTAAC TCGCCTTGAT CGTTGGGAAC CGGAGCTGAA TGAAGCCATA
3961 CCAAACGACG AGCGTGACAC CACGATGCCT GTAGCAATGG CAACAACGTT GCGCAAACTA
4021 TTAACTGGCG AACTACTTAC TCTAGCTTCC CGGCAACAAT TAATAGACTG GATGGAGGCG
4081 GATAAAGTTG CAGGACCACT TCTGCGCTCG GCCCTTCCGG CTGGCTGGTT TATTGCTGAT
4141 AAATCTGGAG CCGGTGAGCG TGGGTCTCGC GGTATCATTG CAGCACTGGG GCCAGATGGT
4201 AAGCCCTCCC GTATCGTAGT TATCTACACG ACGGGGAGTC AGGCAACTAT GGATGAACGA
4261 AATAGACAGA TCGCTGAGAT AGGTGCCTCA CTGATTAAGC ATTGGTAACT GTCAGACCAA
4321 GTTTACTCAT ATATACTTTA GATTGATTTA CCCCGGTTGA TAATCAGAAA AGCCCCAAAA
4381 ACAGGAAGAT TGTATAAGCA AATATTTAAA TTGTAAACGT TAATATTTTG TTAAAATTCG
4441 CGTTAAATTT TTGTTAAATC AGCTCATTTT TTAACCAATA GGCCGAAATC GGCAAAATCC
4501 CTTATAAATC AAAAGAATAG ACCGAGATAG GGTTGAGTGT TGTTCCAGTT TGGAACAAGA
4561 GTCCACTATT AAAGAACGTG GACTCCAACG TCAAAGGGCG AAAAACCGTC TATCAGGGCG
4621 ATGGCCCACT ACGTGAACCA TCACCCAAAT CAAGTTTTTT GGGGTCGAGG TGCCGTAAAG
4681 CACTAAATCG GAACCCTAAA GGGAGCCCCC GATTTAGAGC TTGACGGGGA AAGCCGGCGA
4741 ACGTGGCGAG AAAGGAAGGG AAGAAAGCGA AAGGAGCGGG CGCTAGGGCG CTGGCAAGTG
4801 TAGCGGTCAC GCTGCGCGTA ACCACCACAC CCGCCGCGCT TAATGCGCCG CTACAGGGCG
4861 CGTAAAAGGA TCTAGGTGAA GATCCTTTTT GATAATCTCA TGACCAAAAT CCCTTAACGT
4921 GAGTTTTCGT TCCACTGAGC GTCAGACCCC GTAGAAAAGA TCAAAGGATC TTCTTGAGAT
4981 CCTTTTTTTC TGCGCGTAAT CTGCTGCTTG CAAACAAAAA AACCACCGCT ACCAGCGGTG
5041 GTTTGTTTGC CGGATCAAGA GCTACCAACT CTTTTTCCGA AGGTAACTGG CTTCAGCAGA
5101 GCGCAGATAC CAAATACTGT CCTTCTAGTG TAGCCGTAGT TAGGCCACCA CTTCAAGAAC
5161 TCTGTAGCAC CGCCTACATA CCTCGCTCTG CTAATCCTGT TACCAGTGGC TGCTGCCAGT
5221 GGCGATAAGT CGTGTCTTAC CGGGTTGGAC TCAAGACGAT AGTTACCGGA TAAGGCGCAG
5281 CGGTCGGGCT GAACGGGGGG TTCGTGCACA CAGCCCAGCT TGGAGCGAAC GACCTACACC
5341 GAACTGAGAT ACCTACAGCG TGAGCTATGA GAAAGCGCCA CGCTTCCCGA AGGGAGAAAG
5401 GCGGACAGGT ATCCGGTAAG CGGCAGGGTC GGAACAGGAG AGCGCACGAG GGAGCTTCCA
5461 GGGGGAAACG CCTGGTATCT TTATAGTCCT GTCGGGTTTC GCCACCTCTG ACTTGAGCGT
5521 CGATTTTTGT GATGCTCGTC AGGGGGGCGG AGCCTATGGA AAAACGCCAG CAACGCGGCC
```

FIG. 3-4
pIH1684

5581 TTTTTACGGT TCCTGGCCTT TTGCTGGCCT TTTGCTCACA TGTTCTTTCC TGCGTTATCC
5641 CCTGATTCTG TGGATAACCG TATTACCGCC TTTGAGTGAG CTGATACCGC TCGCCGCAGC
5701 CGAACGACCG AGCGCAGCGA GTCAGTGAGC GAGGAAGCGG AAGAGCGCCT GATGCGGTAT
5761 TTTCTCCTTA CGCATCTGTG CGGTATTTCA CACCGCATAT ATGGTGCACT CTCAGTACAA
5821 TCTGCTCTGA TGCCGCATAG TTAAGCCAGT ATACACTCCG CTATCGCTAC GTGACTGGGT
5881 CATGGCTGCG CCCCGACACC CGCCAACACC CGCTGACGCG CCCTGACGGG CTTGTCTGCT
5941 CCCGGCATCC GCTTACAGAC AAGCTGTGAC CGTCTCCGGG AGCTGCATGT GTCAGAGGTT
6001 TTCACCGTCA TCACCGAAAC GCGCGAGGCA GCTGCGGTAA AGCTCATCAG CGTGGTCGTG
6061 CAGCGATTCA CAGATGTCTG CCTGTTCATC CGCGTCCAGC TCGTTGAGTT TCTCCAGAAG
6121 CGTTAATGTC TGGCTTCTGA TAAAGCGGGC CATGTTAAGG GCGGTTTTTT CCTGTTTGGT
6181 CACTGATGCC TCCGTGTAAG GGGGATTTCT GTTCATGGGG GTAATGATAC CGATGAAACG
6241 AGAGAGGATG CTCACGATAC GGGTTACTGA TGATGAACAT GCCCGGTTAC TGGAACGTTG
6301 TGAGGGTAAA CAACTGGCGG TATGGATGCG GCGGGACCAG AGAAAAATCA CTCAGGGTCA
6361 ATGCCAGCGC TTCGTTAATA CAGATGTAGG TGTTCCACAG GGTAGCCAGC AGCATCCTGC
6421 GATGCAGATC CGGAACATAA TGGTGCAGGG CGCTGACTTC CGCGTTTCCA GACTTTACGA
6481 AACACGGAAA CCGAAGACCA TTCATGTTGT TGCTCAGGTC GCAGACGTTT TGCAGCAGCA
6541 GTCGCTTCAC GTTCGCTCGC GTATCGGTGA TTCATTCTGC TAACCAGTAA GGCAACCCCG
6601 CCAGCCTAGC CGGGTCCTCA ACGACAGGAG CACGATCATG CGCACCCGTG GCCAGGACCC
6661 AACGCTGCCC GAAATT

FIG. 4-1
pIH1873 (SEQ ID NO:18)

```
   1 CCGACACCAT CGAATGGTGC AAAACCTTTC GCGGTATGGC ATGATAGCGC CCGGAAGAGA
  61 GTCAATTCAG GGTGGTGAAT GTGAAACCAG TAACGTTATA CGATGTCGCA GAGTATGCCG
 121 GTGTCTCTTA TCAGACCGTT TCCCGCGTGG TGAACCAGGC CAGCCACGTT TCTGCGAAAA
 181 CGCGGGAAAA AGTGGAAGCG GCGATGGCGG AGCTGAATTA CATTCCCAAC CGCGTGGCAC
 241 AACAACTGGC GGGCAAACAG TCGTTGCTGA TTGGCGTTGC CACCTCCAGT CTGGCCCTGC
 301 ACGCGCCGTC GCAAATTGTC GCGGCGATTA AATCTCGCGC CGATCAACTG GGTGCCAGCG
 361 TGGTGGTGTC GATGGTAGAA CGAAGCGGCG TCGAAGCCTG TAAAGCGGCG GTGCACAATC
 421 TTCTCGCGCA ACGCGTCAGT GGGCTGATCA TTAACTATCC GCTGGATGAC CAGGATGCCA
 481 TTGCTGTGGA AGCTGCCTGC ACTAATGTTC CGGCGTTATT CTTGATGTC TCTGACCAGA
 541 CACCCATCAA CAGTATTATT TTCTCCCATG AAGACGGTAC GCGACTGGGC GTGGAGCATC
 601 TGGTCGCATT GGGTCACCAG CAAATCGCGC TGTTAGCGGG CCCATTAAGT TCTGTCTCGG
 661 CGCGTCTGCG TCTGGCTGGC TGGCATAAAT ATCTCACTCG CAATCAAATT CAGCCGATAG
 721 CGGAACGGGA AGGCGACTGG AGTGCCATGT CCGGTTTTCA ACAAACCATG CAAATGCTGA
 781 ATGAGGGCAT CGTTCCCACT GCGATGCTGG TTGCCAACGA TCAGATGGCG CTGGGCGCAA
 841 TGCGCGCCAT TACCGAGTCC GGGCTGCGCG TTGGTGCGGA TATTTCGGTA GTGGGATACG
 901 ACGATACCGA AGACAGCTCA TGTTATATCC CGCCGTTAAC CACCATCAAA CAGGATTTTC
 961 GCCTGCTGGG GCAAACCAGC GTGGACCGCT TGCTGCAACT CTCTCAGGGC CAGGCGGTGA
1021 AGGGCAATCA GCTGTTGCCC GTCTCACTGG TGAAAAGAAA AACCACCCTG GCGCCCAATA
1081 CGCAAACCGC CTCTCCCCGC GCGTTGGCCG ATTCATTAAT GCAGCTGGCA CGACAGGTTT
1141 CCCGACTGGA AAGCGGGCAG TGAGCGCAAC GCAATTAATG TAAGTTAGCT CACTCATTAG
1201 GCACAATTCT CATGTTTGAC AGCTTATCAT CGACTGCACG GTGCACCAAT GCTTCTGGCG
1261 TCAGGCAGCC ATCGGAAGCT GTGGTATGGC TGTGCAGGTC GTAAATCACT GCATAATTCG
1321 TGTCGCTCAA GGCGCACTCC CGTTCTGGAT AATGTTTTTT GCGCCGACAT CATAACGGTT
1381 CTGGCAAATA TTCTGAAATG AGCTGTTGAC AATTAATCAT CGGCTCGTAT AATGTGTGGA
1441 ATTGTGAGCG GATAACAATT TCACACAGGA AACAGCCAGT CCGTTTAGGT GTTTTCACGA
1501 GCAATTGACC AACAAGGACC ATAGATTATG AAAATCGAAG AAGGTAAACT GGTAATCTGG
1561 ATTAACGGCG ATAAAGGCTA TAACGGTCTC GCTGAAGTCG GTAAGAAATT CGAGAAAGAT
1621 ACCGGAATTA AAGTCACCGT TGAGCATCCG GATAAACTGG AAGAGAAATT CCCACAGGTT
1681 GCGGCAACTG GCGATGGCCC TGACATTATC TTCTGGGCAC ACGACCGCTT TGGTGGCTAC
1741 GCTCAATCTG GCCTGTTGGC TGAAATCACC CCGGACAAAG CGTTCCAGGA CAAGCTGTAT
1801 CCGTTTACCT GGGATGCCGT ACGTTACAAC GGCAAGCTGA TTGCTTACCC GATCGCTGTT
1861 GAAGCGTTAT CGCTGATTTA TAACAAAGAT CTGCTGCCGA ACCCGCCAAA AACCTGGGAA
```

FIG. 4-2
pIH1873

```
1921 GAGATCCCGG CGCTGGATAA AGAACTGAAA GCGAAAGGTA AGAGCGCGCT GATGTTCAAC
1981 CTGCAAGAAC CGTACTTCAC CTGGCCGCTG ATTGCTGCTG ACGGGGGTTA TGCGTTCAAG
2041 TATGAAAACG GCAAGTACGA CATTAAAGAC GTGGGCGTGG ATAACGCTGG CGCGAAAGCG
2101 GGTCTGACCT TCCTGGTTGA CCTGATTAAA AACAAACACA TGAATGCAGA CACCGATTAC
2161 TCCATCGCAG AAGCTGCCTT TAATAAAGGC GAAACAGCGA TGACCATCAA CGGCCCGTGG
2221 GCATGGTCCA ACATCGACAC CAGCAAAGTG AATTATGGTG TAACGGTACT GCCGACCTTC
2281 AAGGGTCAAC CATCCAAACC GTTCGTTGGC GTGCTGAGCG CAGGTATTAA CGCCGCCAGT
2341 CCGAACAAAG AGCTGGCAAA AGAGTTCCTC GAAAACTATC TGCTGACTGA TGAAGGTCTG
2401 GAAGCGGTTA ATAAAGACAA ACCGCTGGGT GCCGTAGCGC TGAAGTCTTA CGAGGAAGAG
2461 TTGGTGAAAG ATCCGCGGAT TGCCGCCACT ATGGAAAACG CCCAGAAAGG TGAAATCATG
2521 CCGAACATCC CGCAGATGTC CGCTTTCTGG TATGCCGTTC GAACTGCGGT GATCAACGCC
2581 GCCAGCGGTC GTCAGACTGT CGATGAAGCC CTGAAAGACG CGCAGACTAA TTCGAGCTCG
2641 AACAACAACA ACAATAACAA TAACAACAAC CTCGGGATCG AGGGAAGGAT TTCACATATG
2701 TCCATGGGCG GCCGCGATAT CGTCGACGGA TCCGAATTCC CTGCAGGTAA TTAAATAAGC
2761 TTCAAATAAA ACGAAAGGCT CAGTCGAAAG ACTGGGCCTT TCGTTTTATC TGTTGTTTGT
2821 CGGTGAACGC TCTCCTGAGT AGGACAAATC CGCCGGGAGC GGATTTGAAC GTTGCGAAGC
2881 AACGGCCCGG AGGGTGGCGG GCAGGACGCC CGCCATAAAC TGCCAGGCAT CAAATTAAGC
2941 AGAAGGCCAT CCTGACGGAT GGCCTTTTTG CGTTTCTACA AACTCTTTCG GTCCGTTGTT
3001 TATTTTTCTA AATACATTCA AATATGTATC CGCTCATGAG ACAATAACCC TGATAAATGC
3061 TTCAATAATA TTGAAAAAGG AAGAGTATGA GTATTCAACA TTTCCGTGTC GCCCTTATTC
3121 CCTTTTTTGC GGCATTTTGC CTTCCTGTTT TTGCTCACCC AGAAACGCTG GTGAAAGTAA
3181 AAGATGCTGA AGATCAGTTG GGTGCACGAG TGGGTTACAT CGAACTGGAT CTCAACAGCG
3241 GTAAGATCCT TGAGAGTTTT CGCCCCGAAG AACGTTTCCC AATGATGAGC ACTTTTAAAG
3301 TTCTGCTATG TGGCGCGGTA TTATCCCGTG TTGACGCCGG GCAAGAGCAA CTCGGTCGCC
3361 ACATACACTA TTCTCAGAAT GACTTGGTTG AGTACTCACC AGTCACAGAA AAGCATCTTA
3421 CGGATGGCAT GACAGTAAGA GAATTATGCA GTGCTGCCAT AACCATGAGT GATAACACTG
3481 CGGCCAACTT ACTTCTGACA ACGATCGGAG GACCGAAGGA GCTAACCGCT TTTTTGCACA
3541 ACATGGGGGA TCATGTAACT CGCCTTGATC GTTGGGAACC GGAGCTGAAT GAAGCCATAC
3601 CAAACGACGA GCGTGACACC ACGATGCCTG TAGCAATGGC AACAACGTTG CGCAAACTAT
3661 TAACTGGCGA ACTACTTACT CTAGCTTCCC GGCAACAATT AATAGACTGG ATGGAGGCGG
3721 ATAAAGTTGC AGGACCACTT CTGCGCTCGG CCCTTCCGGC TGGCTGGTTT ATTGCTGATA
```

FIG. 4-3
pIH1873

```
3781 AATCTGGAGC CGGTGAGCGT GGGTCTCGCG GTATCATTGC AGCACTGGGG CCAGATGGTA
3841 AGCCCTCCCG TATCGTAGTT ATCTACACGA CGGGGAGTCA GGCAACTATG GATGAACGAA
3901 ATAGACAGAT CGCTGAGATA GGTGCCTCAC TGATTAAGCA TTGGTAACTG TCAGACCAAG
3961 TTTACTCATA TATACTTTAG ATTGATTTCC TTAGGACTGA GCGTCAACCC CGTAGAAAAG
4021 ATCAAAGGAT CTTCTTGAGA TCCTTTTTTT CTGCGCGTAA TCTGCTGCTT GCAAACAAAA
4081 AAACCACCGC TACCAGCGGT GGTTTGTTTG CCGGATCAAG AGCTACCAAC TCTTTTTCCG
4141 AAGGTAACTG GCTTCAGCAG AGCGCAGATA CCAAATACTG TCCTTCTAGT GTAGCCGTAG
4201 TTAGGCCACC ACTTCAAGAA CTCTGTAGCA CCGCCTACAT ACCTCGCTCT GCTAATCCTG
4261 TTACCAGTGG CTGCTGCCAG TGGCGATAAG TCGTGTCTTA CCGGGTTGGA CTCAAGACGA
4321 TAGTTACCGG ATAAGGCGCA GCGGTCGGGC TGAACGGGGG GTTCGTGCAC ACAGCCCAGC
4381 TTGGAGCGAA CGACCTACAC CGAACTGAGA TACCTACAGC GTGAGCTATG AGAAAGCGCC
4441 ACGCTTCCCG AAGGGAGAAA GGCGGACAGG TATCCGGTAA GCGGCAGGGT CGGAACAGGA
4501 GAGCGCACGA GGGAGCTTCC AGGGGGAAAC GCCTGGTATC TTTATAGTCC TGTCGGGTTT
4561 CGCCACCTCT GACTTGAGCG TCGATTTTTG TGATGCTCGT CAGGGGGGCG GAGCCTATGG
4621 AAAAACGCCA GCAACGCGGC CTTTTTACGG TTCCTGGCCT TTTGCTGGCC TTTTGCTCAC
4681 ATGTTCTTTC CTGCGTTATC CCCTGATTCT GTGGATAACC GTATTACCGC CTTTGAGTGA
4741 GCTGATACCG CTCGCCGCAG CCGAACGACC GAGCGCAGCG AGTCAGTGAG CGAGGAAGCG
4801 GAAGAGCGCC TGATGCGGTA TTTTCTCCTT ACGCATCTGT GCGGTATTTC ACACCGCATA
4861 TAAGGTGCAC TGTGACTGGG TCATGGCTGC GCCCCGACAC CCGCCAACAC CCGCTGACGC
4921 GCCCTGACGG GCTTGTCTGC TCCCGGCATC CGCTTACAGA CAAGCTGTGA CCGTCTCCGG
4981 GAGCTGCATG TGTCAGAGGT TTTCACCGTC ATCACCGAAA CGCGCGAGGC AGCTGCGGTA
5041 AAGCTCATCA GCGTGGTCGT GCAGCGATTC ACAGATGTCT GCCTGTTCAT CCGCGTCCAG
5101 CTCGTTGAGT TTCTCCAGAA GCGTTAATGT CTGGCTTCTG ATAAAGCGGG CCATGTTAAG
5161 GGCGGTTTTT TCCTGTTTGG TCACTGATGC CTCCGTGTAA GGGGGATTTC TGTTCATGGG
5221 GGTAATGATA CCGATGAAAC GAGAGAGGAT GCTCACGATA CGGGTTACTG ATGATGAACA
5281 TGCCCGGTTA CTGGAACGTT GTGAGGGTAA ACAACTGGCG GTATGGATGC GGCGGGACCA
5341 GAGAAAAATC ACTCAGGGTC AATGCCAGCG CTTCGTTAAT ACAGATGTAG GTGTTCCACA
5401 GGGTAGCCAG CAGCATCCTG CGATGCAGAT CCGGAACATA ATGGTGCAGG GCGCTGACTT
5461 CCGCGTTTCC AGACTTTACG AAACACGGAA ACCGAAGACC ATTCATGTTG TTGCTCAGGT
5521 CGCAGACGTT TTGCAGCAGC AGTCGCTTCA CGTTCGCTCG CGTATCGGTG ATTCATTCTG
5581 CTAACCAGTA AGGCAACCCC GCCAGCCTAG CCGGGTCCTC AACGACAGGA GCACGATCAT
5641 GCGCACCCGT GGCCAGGACC CAACGCTGCC CGAAATT
```

SOLUBILIZATION AND PURIFICATION OF A TARGET PROTEIN FUSED TO A MUTANT MALTOSE-BINDING PROTEIN

CROSS REFERENCE

This application is a §371 application of international application number PCT/US2009/039111 filed on 1 Apr. 2009, herein incorporated by reference.

BACKGROUND

Recombinant proteins have many uses in biotechnology whenever large amounts of pure protein are needed. Microbial expression systems such as *Escherichia coli* (*E. coli*) and yeast are often the first choice due to their low cost and high yield. When expressing foreign proteins in *E. coli*, it is not uncommon to encounter problems of low levels of expression and/or insolubility of the protein. Even if the protein is expressed well and remains soluble, it must be purified from the myriad of other proteins in the cell extract. To facilitate the expression and purification of a target protein, one method that is in common use is to fuse an affinity tag to the protein. A good affinity tag has properties that facilitate high-level expression when fused to the N-terminus of the target protein, and provides a simple one-step affinity purification that allows the target protein to be purified from the expression milieu.

The maltose-binding protein (MBP) of *E. coli* is commonly used as an affinity tag for expression and purification of foreign proteins produced in *E. coli*. The natural role of MBP is to bind maltodextrins at the outer membrane porin and release them to the MalEFK transport apparatus in the inner membrane. Fusion of the C-terminus of MBP to the N-terminus of a target protein permits the expression of the fusion protein in *E. coli* (FIG. 1). MBP and MBP fusions can be purified in a single step by binding to a chromatography matrix containing any of a number of glucose-α1→4-glucose polysaccharides such as amylose, starch or other maltodextrins (U.S. Pat. No. 5,643,758). Many proteins that are soluble in their native host are insoluble when expressed as a recombinant protein. For many of these proteins, fusion to MBP renders them soluble (Kapust & Waugh, *Protein Sci.* 8:1668-74 (1999)).

The utility of MBP as an affinity tag is tempered by the fact that depending on the protein in a MBP-target protein purification, some fusions don't bind to the affinity matrix as well as others. In addition, the presence of non-ionic detergents such as Triton X100 and Tween 20 can interfere with binding, especially for MBP-target protein fusions that have an inherently lower affinity.

Researchers have used the structure of MBP to make directed mutations in order to alter the binding properties of MBP. The X-ray crystal structure of MBP has been reported by Spurlino et al., *J. Biol. Chem.* 266:5202-5219 (1991). MBP consists of two domains, with a cleft between the domains where the polysaccharide binds. The domain that contains the N-terminus is named the domain I, and the domain that contains the C-terminus is named the domain II. Three loops cross between the two domains to form a hinge. Two groups have used the structure to make directed mutations to the region behind the hinges that increase the affinity of MBP for maltose and maltotriose (Marvin et al., *Nature Structural Biology* 8:795-798 (2001); Telmer & Shilton, *Journal of Biol. Chem.* 278:34555-34567 (2003)). However, this approach has an inherent disadvantage, since these modifications to MBP increase the hydrophobicity of the surface of the protein and thus decrease its solubility. This reduces its utility as an affinity tag by increasing its tendency to render a fusion protein insoluble.

SUMMARY

In an embodiment of the invention, a composition is provided which includes a modified maltose-binding protein (MBP) which when fused to a protein results in an increase in binding affinity for maltodextrin compared with the wild type MBP fused to the protein, the modified MBP maintaining enhanced solubility. The modification includes a mutation selected from the group consisting of: F68L, I318V, Q326R, V344M, and $T_{372}TTTITITTTLGIEGR_{387}$ or two or more mutations selected from the group consisting of: F68L, S146T, A313V, I318V, I318A, Q326R, V344M and $T_{372}TTTITITTTLGIEGR_{387}$.

For example, the modification may include a double mutant: A313V and I318V or A313V and I318A.

Examples of MBP amino acid sequences with the mutations described above include SEQ ID NO:8, SEQ ID NO:10, SEQ ID NO:12, SEQ ID NO:14 or SEQ ID NO:16. DNA encoding these modified MBPs are exemplified by SEQ ID NO:7, SEQ ID NO:9, SEQ ID NO:11, SEQ ID NO:13 or SEQ ID NO:15. Vectors containing this DNA and host cells transformed with these vectors are further provided.

The modified MBP may be fused to a target protein to achieve enhanced yield and solubility than would otherwise be possible with the target protein alone.

In an embodiment of the invention, a method of purifying a protein is provided that includes expressing in a host cell, a fusion protein that includes a modified MBP as described above and a target protein. The method further includes permitting the modified MBP fusion protein to bind to a matrix such as a polysaccharide such as maltodextrin and eluting the fusion protein from the matrix in a selected buffer to obtain the purified protein.

In an embodiment of the invention, a method for solubilizing a target protein is provided that includes expressing a modified MBP as described above fused to a target protein so that in vivo, the fusion protein is solubilized to an extent greater than can be observed for the target protein alone.

BRIEF DESCRIPTION OF THE DRAWINGS

FIG. 1 shows a schematic describing the cloning and purification of a target protein by expressing a DNA encoding an MBP fused to a target protein, allowing the fusion protein to selectively bind to amylose, eluting the target protein in a maltose-containing buffer and then recovering the target protein from the purified fusion protein by protease cleavage.

FIG. 2 provides sequences comparing wild-type MBP with modified MBPs.

FIG. 2A: The DNA sequence (SEQ ID NO:1) encoding wild-type MBP (SEQ ID NO:2) from pMAL-c2X.

FIG. 2B: The DNA sequence (SEQ ID NO:3) encoding the MBP mutant A313V (SEQ ID NO:4). Changes in the modified MBP DNA and amino acid sequences are indicated in bold.

FIG. 2C: The DNA sequence (SEQ ID NO:5) encoding the MBP mutant S146T (SEQ ID NO:6). Changes in the modified MBP DNA and amino acid sequences are indicated in bold.

FIG. 2D: The DNA sequence (SEQ ID NO:7) encoding the MBP mutant F68L (SEQ ID NO:8). Changes in the modified MBP DNA and amino acid sequences are indicated in bold.

FIG. 2E: The DNA sequence (SEQ ID NO:9) encoding the MBP mutant I318V (SEQ ID NO:10). Changes in the modified MBP DNA and amino acid sequences are indicated in bold.

FIG. 2F: The DNA sequence (SEQ ID NO:11) encoding the MBP mutant Q326R (SEQ ID NO:12). Changes in the modified MBP DNA and amino acid sequences are indicated in bold.

FIG. 2G: The DNA sequence (SEQ ID NO:13) encoding the MBP mutant V344M (SEQ ID NO:14). Changes in the modified MBP DNA and amino acid sequences are indicated in bold.

FIG. 2H: The DNA sequence (SEQ ID NO:15) of pIH1794, encoding the MBP mutant T/I (SEQ ID NO:16). Changes in the modified MBP DNA and amino acid sequences are indicated in bold.

FIG. 3 provides the sequence of pIH1684 (SEQ ID NO:17).

FIG. 4 provides the sequence of pIH1873 (SEQ ID NO:18).

Lane 1 NEB Protein Ladder
Lane 2. WT MBP crude extract
Lane 3. WT MBP column flow-through
Lane 4. WT MBP eluate
Lane 5. MBP A313V crude extract
Lane 6. MBP A313V column flow-through
Lane 7. WT MBP A313V eluate
Lane 8. MBP A313V I318V crude extract
Lane 6. MBP A313V I318V column flow-through
Lane 10. MBP A313V I318V eluate
Lane 11. MBP A313V I318A crude extract
Lane 12. MBP A313V I318A column flow-through
Lane 13. MBP A313V I318A eluate

DETAILED DESCRIPTION OF THE EMBODIMENTS

Figure 5:
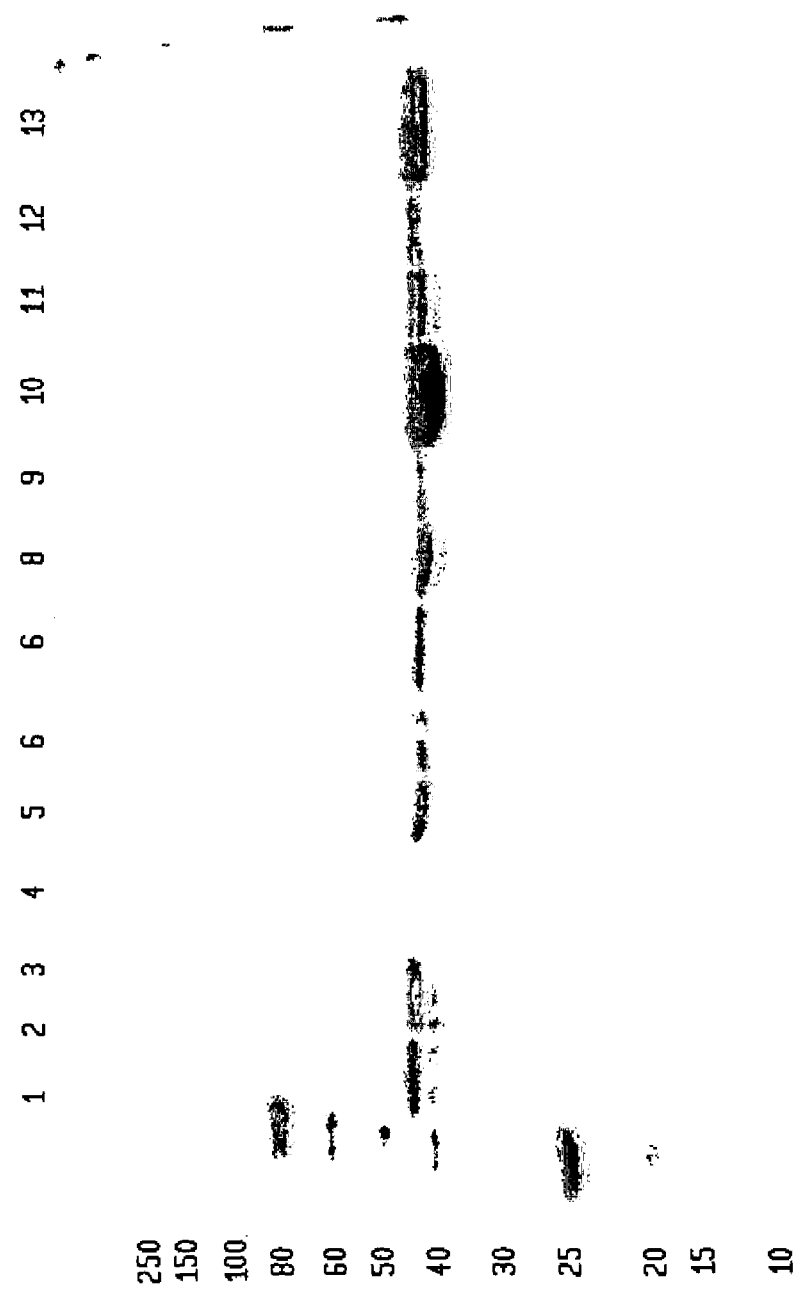
FIG. 5 shows fractions from the amylose affinity purification of MBP on an SDS-PAGE gel. An increase in MBP relative to the other proteins in the crude extract can be seen with the A313V I318V and A313V I318A double mutants, as well as an increase in the ratio of bound MBP vs unbound MBP. Molecular weights of the markers in kDa are shown on the left.
Figure 6:
FIG. 6 shows a crystal structure in which the mutated amino acids of interest are identified. The view is from the opposite side of the binding cleft.

Terms that are used herein are discussed below.

"Wild-type" MBP includes the MBP protein produced by expression from a derivative of one of the pMAL-2 plasmids that has a stop codon in the polylinker, for example pKO1483.

"Enhanced solubility of a protein fused to a mutant MBP" is an increase in the amount of soluble protein when compared to that same protein in the absence of MBP. Solubility can be expressed as the ratio of soluble protein to the total amount of that protein present before insoluble material is removed, for example by centrifugation.

"Increased affinity of a mutant MBP" or "mutant MBP fusion protein" includes an increase in the amount of protein that binds to a solid substrate such as a maltodextrin under a defined set of conditions. The efficacy of the affinity purification can be expressed as the ratio of protein that binds to maltodextrin under the specified conditions and is then eluted with a specified buffer to the total amount of that protein applied to the column.

The present embodiments of the invention provide MBP mutants which when fused to a target protein maintain or enhance the solubility of the fusion protein during expression in vivo and can also improve the affinity of the fusion protein during purification.

In embodiments of the invention, mutant MBPs show increased binding to a polysaccharide, such as a maltodextrin attached to a matrix, compared to wild type MBPs. The modified MBPs can then eluted from the matrix using a solution of, for example, a soluble maltodextrin, yielding at least 1.3 to 10-fold more protein when compared to wild-type MBP.

In order to discover these improved mutants of MBP, technical hurdles had to be overcome which include developing techniques which enable a large number of samples to be handled. This required improved methods for breaking up host cells to release solubilized fusion protein where sonication is not practical for large scale purification and lysis buffers could interfere with affinity binding of MBP. It was discovered that by titrating the detergent and the lysozyme, it was possible to identify the appropriate concentration and ratio of these lysis reagents to effectively break up host cells without negatively impacting binding affinity.

In an embodiment of the invention, screening for mutants with desired binding affinity properties was performed using 96 well microplates where each well contained a micro matrix for binding fusion protein and a filter apparatus removed contaminating materials in the filtrate. This made possible rapid screening of large numbers of samples. Such screening methods for obtaining and testing modified mutant MBP proteins as improved tags for purifying proteins are described in the examples. Modified MBPs that have increased affinity for a matrix solve the problem associated with wild-type MBP of MBP fusions proteins that bind poorly to a matrix or where binding is disrupted by the presence of non-ionic detergent.

In the examples, seven mutations (F68L, S146T, A313V, I318V, Q326R, V344M, and a modified spacer at the C-terminus of MBP) are described with the desired properties of enhanced solubility and improved binding affinity to a polysaccharide matrix. The A313V and I318V mutations described herein are located in and near the third hinge that crosses between the two domains, specifically, in the loop between helices XI and XII. The F68L mutation is in β-sheet C in domain I, adjacent to the maltose-binding site. The V244M mutation is in helix XIII in domain II, and is adjacent to the maltose-binding site on the opposing side. Q326R is in helix XII in domain II, on a surface that contacts domain I in the open conformation. These mutations enhance both the solubility and increase the affinity of fusion proteins. When expressing foreign proteins in *E. coli*, the recombinant protein may be partially or completely expressed in the form of insoluble aggregates. This problem is resolved using mutant MBPs described here. In particular examples, solubility may be increased by 1.05 or greater upwards with an upper limit of total solubility.

In an embodiment of the invention, a micromatrix formed from maltodextrin chemically linked to agarose beads was used in a 96 well plate. However, any suitably shaped matrix may be formed from any matrix material known in the art that can be chemically linked to maltodextrin or any other substrate suitable for binding wild type MBP and MBP mutants (see for example Uy and Wold, *Anal. Biochem.* 81:98-107 (1977)).

All references cited herein, as well as U.S. provisional application No. 60/792,133 filed Apr. 14, 2006 and WO 2007/120809 are incorporated by reference.

EXAMPLES

Materials

Restriction enzymes, β-agarase, DNA polymerases, T4 ligase, Antarctic phosphatase, Litmus 38, the pMAL Protein Fusion and Purification System including pMAL-c2X and pMAL-c2G, amylose resin (#E8021), anti-MBP monoclonal antibody linked to horse radish peroxidase (#E8038), the USER Friendly Cloning kit, the *K. lactis* Protein Expression Kit including the vector pKLAC1, host strains TB1, ER1992, ER2502, ER2984, NEB 5-alpha, and NEB Turbo, and synthetic oligonucleotides were obtained from New England Biolabs, Inc. (NEB), Ipswich, Mass. Unifilter 800 microtiter microplates with filter bottoms were purchased from Whatman, Brentford, England. The Minelute DNA Extraction and Qiaprep Spin kits were purchased from Qiagen, Valencia, Calif. Mega 10 was purchased from Dojindo, Gaithersburg, Md. Hen egg white lysozyme, Coomassie brilliant blue R and acid washed glass beads (425-600 micron) were purchased from Sigma-Aldrich, St. Louis, Mo. Sea Plaque GTG low melting temperature agarose was purchased from Cambrex, E. Rutherford, N.J. Disposable polypropylene columns (#732-6008) were purchased from BioRad, Hercules, Calif. 10-20% gradient gels were purchased from either Daiichi, Tokyo, Japan or InVitrogen/Novex, Carlsbad, Calif. The Complete™ protease inhibitor cocktail was purchased from Roche, Basel, Switzerland. SimplyBlue Safestain was purchased from Invitrogen, Carlsbad, Calif. The human dihydrofolate reductase (DHFR) cDNA clone pOTB7-DHFR was purchased from Invitrogen (MGC:857). The GAPDH gene was obtained from pJF931 (Fox et al. *FEBS Lett.* 537:53-57 (2003)).

Techniques

The *Serracia marscesens* nuclease was obtained as described in WO06/020868. Minipreps of plasmid DNA were prepared using the Qiaprep Spin kit. Random PCR mutagenesis was carried out as described in Fromant et al. (*Analytical Biochemistry* 224, 347-353 (1995)). PCR was carried out using Vent® DNA polymerase except as noted. DNA fragments were gel-purified by electrophoresis on 1% Sea Plaque GTG low melting temperature agarose, cutting out the band, and either purifying the DNA using the Minelute DNA Extraction kit, or melting it at 75° C. for 5 minutes, cooling to 37° C., and digesting with β-agarase for 1-2 h. DNA sequencing was performed on Applied Biosystemss (ABIs) automated DNA Sequencer model 3100 ABI, using Big Dye labeled dye-terminator chemistry (ABI, Foster City, Calif.). SDS-PAGE was carried out according to the instructions of the acrylamide gel provider, and proteins were visualized by staining with Coomassie brilliant blue R except where noted otherwise.

MBP was expressed from either pMal-c2X or pMal-c2G or a derivative of pMal-c2G. The numbering of bases to identify mutations in malE refers to the base number in the pMAL-c2X sequence (FIGS. 2A-1, 2A-2, 2B-1, 2B-2, 2C-1, 2C-2, 2D-1, 2D-2, 2E-1, 2E-2, 2F-1, 2F-2, 2G-1, 2G-2, 2H-1, 2H-2 (SEQ ID NOS:1-16). The pMAL-c2G derivative pSN1578 was created by cleaving the plasmid with BsmI and BsiWI, treating the product with DNA polymerase Klenow fragment plus all four dNTPs, followed by ligation to create a deletion within the malE gene.

Site-directed mutagenesis was carried out using a four primer PCR mutagenesis as described in Guan et al. (*Nucleic Acid Research*, 33:6225-6234 (2005)). MBP and MBP fusion proteins were purified as described in the instructions for the pMAL Protein Fusion and Purification System, except that in some cases, cells were lysed with a lysozyme/detergent solution instead of sonication.

Large-scale purifications were carried out with crude cell extract prepared from 500 to 1000 mL of culture, and loaded on a 2.5 cm diameter column containing 15 ml of amylose resin (NEB #E8021, Ipswich, Mass.). Small-scale purifications were carried out with crude extract prepared from 67 ml of culture, and loaded on a disposable polypropylene column containing 1 ml of amylose resin. SDS-polyacrylamide gel electrophoresis was carried out using 10-20% gradient gels. For quantitation of gel bands, gels were dried between cellophane sheets and scanned using a Microtek III scanner Microtek, Carson, Calif., and densitometry carried out using Image J (NIH).

Example I

Isolation of Mutants in MBP with Improved Properties

Screening for Improved Yield after Purification

Random mutagenesis of the malE gene from pMAL-c2x was achieved by error-prone PCR using the primers:
oligo 1: 5' GGAGACAUGAATTCAATGAAAATCGAA-GAA (SEQ ID NO:19), and oligo 2:
5' GGGAAAGUAAGCTTAATCCTTCCCTCGATC (SEQ ID NO:20). PCR fragments were cloned into linearized pNEB208A using the USER Friendly Cloning Kit, following the manufacturer's instructions. Transformants were grown overnight in 1 mL LB+1 mM IPTG and 100 µg/ml ampicillin, then lysed by adding 0.3 mg/mL lysozyme and 20 units of the *S. marscens* nuclease, incubating for 10 min, then adding 0.1 ml of 2% Tween 20.

The crude extracts were applied to a 50 µL amylose resin column (NEB #E8021, Ipswich, Mass.) in a Unifilter 800 microplate, and each well was washed with 0.7 ml of 20 mM Tris-Cl, 0.2 M NaCl, 1 mM EDTA, pH 7.4 (column buffer), then with 0.7 mL of 10 mM sodium phosphate, 0.2 M NaCl, 1 mM EDTA, pH 7.2. The protein bound to the amylose resin was then eluted with 0.2 mL of 10 mM maltose, 10 mM sodium phosphate, 0.2 M NaCl, 1 mM EDTA, pH 7.2. The eluate was transferred to an Immulon 2HB microtiter plate (ThermoFisher Scientific, Waltham, Mass.) and incubated overnight at 4° C. The microtiter wells were then emptied, washed twice with 20 mM Tris-Cl, 150 mM NaCl, pH 7.5 (TBST), then blocked with 0.36 ml TBST+3% bovine serum albumin for 1 h at 37° C.

The wells were washed twice with TBST, then 0.1 ml of a 1:2000 dilution of anti-MBP monoclonal antibody linked to horse radish peroxidase in TBST+3% bovine serum albumin was added to each well and the plate incubated at 37° C. for 1 h. The wells were emptied, then washed twice with TBST. The wells were developed with 0.01% o-phenylenediamine, 0.003% hydrogen peroxide in water. The detection reaction was stopped by adding 0.025 mL 4 M $H_2SO_4$, and wells were assayed spectrophotometrically at 490 nm. Cells were recovered from lysates corresponding to samples that showed higher binding and elution as compared to wild-type MBP. These candidates were grown and retested to confirm the higher binding and elution.

Characterization and Separation of Mutations Obtained after Random Mutagenesis

Two isolates from a library in USER having increased binding and elution profiles were sequenced (FIG. 2). One isolate, G8-1, was found to have a single mis-sense mutation, G1964C, along with a silent mutation. The G1964C mutation corresponds to the amino acid change S146T in MBP. The other isolate, A9, was found to have three mis-sense mutations, A1583G, A2419G and C2465T, along with a silent mutation. The A1583G, A2419G and C2465T mutations correspond to the amino acid changes N195, K298E and A313V, respectively.

Subcloning into pMal-C2X or pSN1578

Each isolate was amplified by PCR with the following primers: oligo 3:
5' GACTCATATGAAAATCGAAGAAGG-TAAACTGGTAATCTGGATTAACGGC (SEQ ID NO:21) and oligo 4:
5' ATATAAGCTTTCACCTTCCCTCGATCCCGAGGT (SEQ ID NO:22). The amplified DNA was ethanol precipitated, cut with NdeI and HindIII in NEBuffer 4 (NEB, Ipswich, Mass.), and gel purified. pSN1578 was cleaved with NdeI and HindIII and the vector backbone was gel purified. The G8-1 and A9 fragments were mixed with the pSN1578 fragment and ligated, and the ligation was used to transform TB1. A plasmid preparation from each transformant was sequenced and named pIH1596 for G8-1 and pIH1593 for A9. The 3' primer in this experiment had a stop codon in the correct reading frame to prevent malE translation from proceeding into the lacZα fragment of pMAL. Thus, these subclones produced a modified MBP that ended after the amino acid sequence IEGR encoded by the polylinker. A control plasmid containing a wild-type malE gene followed by a stop codon was constructed by cleaving pMAL-c2X in the polylinker between malE and lacZα with XbaI. The XbaI overhang was filled in using DNA polymerase I, large fragment (Klenow) and all four dNTPs, then the plasmid was recircularized by treatment with T4 ligase. This introduces a stop codon in the same reading frame as malE, and this derivative produced an MBP comparable to that produced by G8-1 and A9, except for an 8 residue extension encoded by the polylinker. This control plasmid was named pKO1483. $E.\ coli$ TB1 containing pKO1483, pIH1596 and pIH1593 were grown in a 500 mL culture of LB+0.1% glucose and 100 μg/ml ampicillin to $2\times10^8$ cells/ml, induced with 0.3 mM IPTG, grown for 2 h at 37° C., then harvested. The cells were resuspended in 25 ml column buffer (0.2 mL of 10 mM maltose, 10 mM sodium phosphate, 0.2 M NaCl, 1 mM EDTA, pH 7.2)+10 mM β-mercaptoethanol, then lysed by sonication. The extract was clarified by centrifuging at 9000×g for 30 min, then diluted 1:4 with column buffer and loaded onto a 15 ml column of amylose resin. The column was washed with about 125 mL column buffer, and eluted with column buffer+10 mM maltose. The yields of MBP were compared among the three strains (Table 1). The results confirm that the modified MBPs showed an increased binding to amylose and elution in appropriate buffers.

In order to ascertain which of the three mutation(s) were necessary for increased binding of the A9 variant, the three mutations were subcloned separately into pSN1578, a pMAL-c2G derivative with a deletion internal to the malE gene (which allows easy identification of clones that received an insert). The A1583G and A2419G mutations either had no effect or reduced the yield of MBP in the affinity purification, and were discarded. The C2465T mutation was recreated in isolation by 4 primer site-directed PCR mutagenesis using pMAL-c2X as the first template, with the primers oligo 5: 5' CTTCAAGGGTCAACCATCCAAACC (SEQ ID NO:23) and oligo 6: 5' AATACGCGGATCTTTCACCAACTCTTC (SEQ ID NO:24) to create the N-terminal PCR fragment, and with primers oligo 7: 5' GAAGAGTTGGTGAAAGATC-CGCGTATT (SEQ ID NO:25) and oligo 8: 5' CTGAGAAT-TCTGAAATCCTTCCCTCGAT (SEQ ID NO:26) to create the C-terminal PCR fragment. The assembly step was carried out with the gel-purified N- and C-terminal fragments as the template and the primers oligo 5 and oligo 8. The final PCR fragment was cut with BlpI and AvaI, gel purified, and ligated to pMAL-c2X that had been cut with BlpI and AvaI and gel purified. The ligation was used to transform TB1, and plasmid was purified from the transformants and sequenced to confirm the C2465T mutation. An isolate was chosen for further study and named pIH1606.

In the construction of pIH1606, the stop codon at the end of MBP was not conserved. This construct expressedMBP fused to the LacZα fragment. In order to compare the effect of the C2465T mutation to its parent, A9, a stop codon was introduced after the malE gene in pIH1606. The plasmid was cleaved with XbaI, filled in with Klenow plus dNTPs, and religated as described above for pKO1483. The C2465T derivative with a stop codon was called pPR1610. Large scale MBP purifications of TB1 bearing this plasmid, in parallel with pKO1483 and A9, showed that all of the increase in yield of MBP found in A9 could be accounted for by the C2465T mutation. This mutation changed alanine 313 of MBP to a valine (A313V).

In order to be able to compare MBP (S146T) to wild-type MBP and MBP (A313V) in derivatives that have exactly parallel construction, a version of MBP (S146T) was constructed that had the same stop codon as pKO1483 was constructed. An NdeI, BlpI fragment from pIH1596 was purified and subcloned into pKO1493 cut with NdeI and BlpI, creating pIH1619.

Example II

Additional MBP Mutants with Improved Binding

Additional mutants of MBP were generated by the method in Example I, with a few modifications. To avoid the step of subcloning the malE insert from the USER plasmid pNEB208A to pMal-C2X or pSN1578, a pMAL vector with an MfeI site between the tac promoter and the malE ribosome-binding site was constructed to be the recipient of the PCR fragments, named pIH1684 (FIG. 3; SEQ ID NO:17). Error-prone PCR was carried out as described above with the primers oligo 9: 5' CACGAGCAATTGACCAACAAGGAC (SEQ ID NO:27) and oligo 10: 5' GATCGAGAGCTC-GAATTAGTCTGC (SEQ ID NO:28). Both the PCR product and pIH1684 were cut with MfeI and SacI and gel purified. The two fragments were ligated together and the ligation was used to transform ER2523, and the transformants were pooled and stored at −80° C. For each round of screening, the pool was diluted and plated to give single colonies on LB amp Single colonies were used to inoculate 1 ml cultures, and the cultures were lysed and screened for increased yield in the amylose resin affinity purification as described in Example 1. Five additional isolates were recovered: 2E8, 3F9, 15F5, 24G7, and 33D12. 2E8 contained the mutations C1894A (encoding L123M), C2333T (encoding A269V), and a deletion of T2628 that altered the reading frame from codon 368 to the end of the gene. The isolates 3F9, 15F5 and 24G7 each contained a single mutation, A2504G (encoding Q326R), T1729C (encoding F68L), and A2479G (encoding I318V), respectively. The plasmids carrying these mutations were called pIH1732 for Q326R, pIH1733 for F68L and pIH1743 for I318V. The isolate 33D12 contained the mutations C1907T (encoding P127V), C2018T (encoding A164V), A2351G (encoding E275G), G2482A (encoding A319T) and G2557A (encoding V344M). The mutations in 2E8 and 33D12 were separated as follows, in a process similar to that described for A9 in Example 1, and mutations that did not improve the purification properties of MBP were discarded.

The V344M mutation from 33D12 was recreated in isolation by 4 primer site-directed PCR mutagenesis using pIH1684 as the first template, with the primers oligo 11: 5' CCGACCTTCAAGGGTCAACCATCC (SEQ ID NO:29) and oligo 13: 5' CCGCAGTACGCATGGCATACCAGA (SEQ ID NO:30) to create the N-terminal PCR fragment, and with primers oligo 13: 5' TCTGGTATGCCATGCGTACT-GCGG (SEQ ID NO:31) and oligo 14: 5' CGC-CAGGGTTTTCCCAGTCACGAC (SEQ ID NO:32) to create the C-terminal PCR fragment. The assembly step was carried out with the gel-purified N- and C-terminal fragments as the template and the primers oligo 11 and oligo 14. The final PCR fragment was cut with BlpI and HindIII, gel purified, and ligated to pIH1684 that had been cut with BlpI and HindIII and gel purified. The ligation was used to transform ER2523, and miniprep DNA was prepared from several transformants. An isolate was sequenced to confirm the G2557A mutation and saved as pIH1822.

The deletion of T2628 changed the reading frame of the spacer present downstream of the MBP in the pMAL vectors. The original sequence read NSSS(N)$_{10}$LGIEGR, while the frame-shifted sequence read IRAR(T)$_4$ITI(T)$_3$ SGSREG. These changes were arbitrarily divided into two categories, the changes from (N)$_{10}$ to (T)$_4$ITI(T)$_3$ and the changes before and after this sequence. Testing determined that changing just the (N)$_{10}$ region to the T/I sequence, i.e. to NSSS(T)$_4$ITI(T)$_3$LGIEGR, most improved the purification properties of MBP. The T/I spacer was inserted into pIH1684 by cleaving pIH1684 with SacI and AvaI and adding an annealed mixture of oligo 15: 5' CAACTACTACCACCATAAC-TATAACCACTACCC (SEQ ID NO:33) and oligo 16: 5' CCGAGGGTAGTGGTTATAGTTATGGTGG-TAGTAGTTGAGCT (SEQ ID NO:34). The mixture was ligated and used to transform ER2523, and plasmid was isolated from one transformant and the sequence confirmed. The plasmid was named pIH1794, and the MBP encoded by this construct was called MBP T/I.

Each of the mutant MBP plasmids was used to make a derivative expressing the MBP-CBD fusion protein as follows. Plasmids pIH1732, pIH1733 and pIH1743 were cut with SacI and HindIII, and the backbone fragment was gel purified. Plasmid pMB50 (see published patent WO2007/120809) was cut with SacI and HindIII, and the CBD fragment was gel purified. The fragment for each pMAL mutant plasmid was mixed with the CBD fragment, ligated, and the ligation mixture was used to transform ER2523. Plasmid DNA was isolated from several transformants, and the correct structure confirmed by sequencing. The pIH1732 (Q326R) derivative was named pIH1759, the pIH1733 (F68L) derivative was named pIH1767, and the pIH1743 (I318V) derivative was named pIH1769. For the remaining two mutations, the CBD insert was prepared by PCR using oligo 17: 5' ACTACCCTCGGGATCGAGGGAAGGGG-TACGCTTGAAGGTTCTCAGCATG CAC (SEQ ID NO:35) and oligo 14, with pMB50 as the template. The PCR fragment was ethanol precipitated, resuspended and cut with AvaI and HindIII. The pIH1794 and pIH1822 plasmids were cut with AvaI and HindIII, the backbone fragments were gel purified, then mixed with the CBD fragment and ligated. The ligation mixture was used to transform ER2523. Plasmid DNA was isolated from several transformants, and the correct structure confirmed by sequencing. The pIH1794 (T/I) derivative was named pIH1845, and the pIH1822 (V344M) derivative was named pIH1855.

Each of the mutant MBP plasmids was used to make a derivative expressing the MBP-DHFR fusion protein as follows. Plasmids pIH1732, pIH1733 and pIH1743 were cut with AvaI and SbfI, and the backbone fragment was gel purified. Plasmid pIH1616 (see published patent WO2007/120809) was cut with AvaI and SbfI, and the DHFR fragment was gel purified. The fragment for each pMAL mutant plasmid was mixed with the DHFR fragment, ligated, and the ligation mixture was used to transform ER2523. Plasmid DNA was isolated from several transformants, and the correct structure confirmed by sequencing. The pIH1732 (Q326R) derivative was named pIH1772, the pIH1733 (F68L) derivative was named pIH1773, and the pIH1743 (I318V) derivative was named pIH1765. For the remaining two mutations, the DHFR insert was prepared by PCR using oligo 18: 5' GGTCGTCAGACTGTCGATGAAGCC (SEQ ID NO: 36) and oligo 14, with pIH1616 as the template. The PCR fragment was ethanol precipitated, resuspended and cut with AvaI and HindIII. The pIH1794 and pIH1822 plasmids were cut with AvaI and HindIII, the backbone fragments were gel purified, then mixed with the CBD fragment and ligated. The ligation mixture was used to transform ER2523. Plasmid DNA was isolated from several transformants, and the correct structure confirmed by sequencing. The pIH1794 (T/I) derivative was named pIH1816, and the pIH1822 (V344M) derivative was named pIH1856.

Small scale purifications were carried out using strains bearing the constructs described above. The results were normalized to yield per liter of culture, and are presented in Table 2. The additional mutants gave yields of between 1.3-fold and 8.0-fold higher than wild-type for unfused MBP, and between 1.5-fold and 7.9-fold higher for MBP-CBD. In order to test the effect of the mutations on the ability of MBP to enhance the solubility of DHFR, cells bearing the plasmids that encoded the corresponding MBP-DHFR fusions were grown, induced, sonicated, and the extracts separated into soluble and insoluble fractions. The fractions were run on SDS-PAGE, the gels scanned, and the amount of MBP-DHFR was quantitated using ImageJ. The results are presented in Table 3. All of the additional mutants except MBP T/I maintained or increased the ability of MBP to enhance the solubility of DHFR. MBP T/I maintained nearly all of MBPs solubility enhancement.

In order to test whether the mutations could be combined to give even higher yields, a plasmid with the A313V mutation was constructed with convenient restriction sites so that a synthetic cassette containing a second downstream mutation could be added. The plasmid was named pIH1873, and its sequence is shown in FIG. 4 (SEQ ID NO:18). This plasmid had a SacII site following the A313V mutation, and a BstBI site 94 bases downstream of the A313V mutation. The double mutant A313V, I318V was constructed by first creating a cassette with the I318V mutation. The oligo 19: 5' AGATC-CGCGGGTTGCCGCCACTATG (SEQ ID NO:37) and oligo 20: 5' GCAGTTCGAACGGCATACCAGAAAGCG-GACATCTGCGGGATGTTCGGCA TGATTTCAC-CTTTCTGGGCGTTTTCCATAGTGGCG-GCAACCCGCGGATCT (SEQ ID NO:38) were annealed, then filled in with Phusion polymerase plus all four dNTPs. The resulting DNA product was cleaved with SacII and BstBI, mixed with pIH1873 that had been cleaved with SacII and BstBI, and the mixture was ligated. The ligation was used to transform ER2523, and DNA was prepared from an isolate and sequenced to confirm the expected structure. The plasmid with the two mutations A313V and I318V was named pIH1877.

In order to see if other substitutions for I318 would also improve the affinity tag properties of MBP, a second plasmid was constructed with the mutations A313V and I318A. The oligo 21: 5'AGATCCGCGGGCAGCCGCCACTATG (SEQ ID NO:39) and oligo 22: 5' GCAGTTCGAACGGCATAC-CAGAAAGCGGACATCTGCGGGATGTTCGGCA TGATTTCACCTTTCTGGGCGTTTTCCAT-AGTGGCGGCTGCCCGCGGATCT (SEQ ID NO:40) were annealed, then filled in with Phusion polymerase plus all four dNTPs. The resulting DNA product was cleaved with SacII and BstBI, mixed with pIH1873 that had been cleaved with SacII and BstBI, and the mixture was ligated. The ligation was used to transform ER2523, and DNA was prepared from an isolate and sequenced to confirm the expected structure. The plasmid with the two mutations A313V and I318A was named pIH1878.

In order to test whether the double mutant MBPs could improve the yield of MBP-CBD fusion protein, the CBD gene was inserted into pIH1877 and pIH1878 as follows. The CBD insert was prepared by performing a PCR on the gene using oligos 18 and 14 and the template pIH1875, the PCR product was cut with AvaI and HindIII and then gel purified. The plasmids pIH1877 and pIH1878 were cleaved with AvaI and HindIII, and the backbone fragments gel purified. The plasmid fragments were mixed with the insert and ligated, and the ligation was used to transform ER2523. DNA was prepared from transformants and the correct structure was confirmed by sequencing. The plasmid encoding MBP(A313V, I318V)-CBD was named pIH1901 and the plasmid encoding MBP (A313V, I318A)-CBD was named pIH1902.

ER2523 bearing pIH1877, pIH1878, pIH1901 and pIH1902 were grown, induced, crude extracts were prepared, and protein was purified on 1 ml amylose columns. The results are presented in Table 4. For MBP, the double mutant MBPs increased the yield in the affinity purification 11-fold for MBP(A313V, I318V) and 6-fold for MBP(A313V I318A). For MBP-CBD, the double mutants increased the yield 12-fold for MBP(A313V I318V)-CBD and 6-fold for MBP(A313V I318A)-CBD. Unexpectedly, the cells bearing the double mutants expressed MBP as a higher fraction of the total protein when compared to wild-type MBP (FIG. 5). In order to test whether the increase in yield was due to an increase in binding affinity or simply an increase in the amount of MBP loaded on the column, gel lanes of wild-type and double mutant crude extract were scanned and quantitated, and a second set of affinity purifications was carried out where the amount of crude extract from the double mutants was normalized so that the total amount of MBP loaded on the column was the same as for wild type. The results are shown in the last two lines of Table 4. Normalizing the amount of MBP loaded did not decrease the yield, indicating that the increased yield relative to wild-type was due to increased affinity of the MBP double mutant. In fact, these purifications yielded even more protein, probably due to the increased dilution of the crude extract, which reduced the interference from other components in the extract which bind non-specifically.

In order to test whether the double mutant MBPs maintained the ability of MBP to enhance the solubility of aggregation-prone proteins, derivatives expressing MBP-DHFR were constructed. The DHFR insert was prepared by PCR using oligos 18 and 14 as primers and pIH1616 as a template. The PCR fragment was cleaved with AvaI and HindIII and gel purified. The plasmids pIH1877 and pIH1878 were cleaved with AvaI and HindIII, and the backbone fragment was gel purified. The plasmid fragments were mixed with the DHFR insert and ligated, and the ligations were used to transform ER2523. DNA was prepared from the transformants, and the correct structure was confirmed by sequencing. The plasmid encoding MBP(A313V I318V)-DHFR was named pIH1891, and the plasmid encoding MBP(A313V I318A)-DHFR was named pIH1892. Cells bearing these plasmids were grown, induced, sonicated, and the extracts separated into soluble and insoluble fractions. The fractions were run on SDS-PAGE, the gels scanned, and the amount of MBP-DHFR was quantitated using ImageJ. The results are presented in Table 5. The double mutants showed an increased ability to enhance the solubility of DHFR as compared to wild-type MBP.

TABLE 1

Yield of MBP-Klenow for wild-type and modified MBPs*

| Derivative | MBP-Klenow Yield (mg/L) | MBP-CBD Yield (mg/L) | MBP-DHFR Solubility Soluble sol. + insol. |
|---|---|---|---|
| WT | 0.7 mgs | 13.2 | 36% |
| S146T | 2 mgs | ND | 67% |
| A313V | 0.7 mgs | 21.8 | 67% |

*data from published patent WO2007/120809; yields and solubility are given for experiments carried out in parallel for MBP wild-type and each derivative; ND not determined.

TABLE 2

Relative yield of MBP and MBP-CBD for additional mutants*

| | MBP | | MBP-CBD | |
|---|---|---|---|---|
| Derivative | Plasmid | Yield (mg/L) | Plasmid | Yield (mg/L) |
| WT | pIH1684 | 2.3 | pIH1560 | 3.5 |
| F68L | pIH1733 | 4.2 | pIH1767 | 8.3 |
| I318V | pIH1743 | 5.5 | pIH1765 | 27.8 |
| Q326R | pIH1732 | 2.9 | pIH1772 | 7.5 |
| V344M | pIH1822 | 4.3 | pIH1855 | 5.1 |
| T/I | pIH1794 | 18.5 | pIH1845 | 5.1 |

*yields are given for experiments carried out in parallel for MBP wild-type and each derivative.

TABLE 3

Solubility of MBP-DHFR for additional mutants*

| Derivative | Plasmid | % Soluble |
|---|---|---|
| WT | pIH1616 | 59% |
| F68L | pIH1773 | 62% |
| I318V | pIH1765 | 62% |
| Q326R | pIH1772 | 81% |
| V344M | pIH1856 | 67% |
| T/I | pIH1816 | 48% |

*solubility is given for experiments carried out in parallel for MBP wild-type and each derivative.

TABLE 4

Relative yield of MBP and MBP-CBD for double mutants; "–N" indicates amount of crude extract used was normalized to load equal amounts of MBP to the wild-type sample

| | MBP | | MBP-CBD | |
|---|---|---|---|---|
| Derivative | Plasmid | Yield (mg/L) | Plasmid | Yield (mg/L) |
| WT | pIH1684 | 2.3 | pIH1560 | 3.5 |
| A313V I318V | pIH1877 | 22.8 | pIH1901 | 43.9 |
| A313V I318A | pIH1878 | 12.7 | pIH1902 | 21.6 |
| A313V I318V-N | pIH1877 | 35.8 | | |
| A313V I318A-N | pIH1878 | 17.3 | | |

TABLE 5

Solubility of MBP-DHFR for double mutants

| Derivative | Plasmid | % Soluble |
|---|---|---|
| WT | pIH1616 | 59% |
| A313V I318V | pIH1891 | 61% |
| A313V I318A | pIH1892 | 71% |

What is claimed is:

1. A composition, comprising: a modified maltose-binding protein (MBP), the modified MBP comprising a mutation at a position selected from the group consisting of: F68, I318, Q326, V344, and T372TTTITITTTLGIEGR387; or two or more mutations selected from the group consisting of: F68, S146, A313, I318, Q326, V344 and T372TTTITITTTLGIEGR387, wherein the modified maltose-binding protein does not consist of a mutation only at S146 and A313, and wherein the identified positions of the mutations correspond to amino acid positions in wildtype MBP having an amino acid sequence corresponding to SEQ ID NO:2.

2. A composition according to claim 1, wherein the modification comprises A313V and I318V.

3. A composition according to claim 1, wherein the modification comprises A313V and I318A.

4. A composition according to claim 1, fused to a target protein to form a fusion protein.

5. A composition according to claim 1, comprising: SEQ ID NO:8, SEQ ID NO:10, SEQ ID NO:12, SEQ ID NO:14 or SEQ ID NO:16.

6. A composition according to claim 1, wherein the modification further comprises a mutation selected from the group consisting of: F68L, I318V, I318A, Q326R, V344M, and T372TTTITITTTLGIEGR387; or two or more mutations selected from the group consisting of: F68L, S146T, A313V, I318V, I318A, Q326R, V344M and 372TTTITITTTLGIEGR387.

7. An isolated DNA encoding a modified MBP according to claim 1, comprising: SEQ ID NO:7, SEQ ID NO:9, SEQ ID NO:11, SEQ ID NO:13 or SEQ ID NO:15.

8. A vector comprising a DNA according to claim 7.

9. A host cell transformed with a vector according to claim 7.

10. A method of purifying a protein comprising:
expressing in a host cell, a fusion protein comprising a modified MBP according to claim 1 and a target protein;
permitting the modified MBP fusion protein to bind to a matrix; and
eluting the fusion protein from the matrix in a selected buffer to obtain the purified protein.

11. A method according to claim 10, wherein the matrix is a polysaccharide.

12. A method according to claim 11, wherein the polysaccharide is a maltodextrin.

13. A method according to claim 10, wherein the modified MBP comprises: SEQ ID NO:8, SEQ ID NO:10, SEQ ID NO:12, SEQ ID NO:14 or SEQ ID NO:16.

14. A method according to claim 10, wherein the modified MBP is encoded by: SEQ ID NO:7, SEQ ID NO:9, SEQ ID NO:11, SEQ ID NO:13 or NO:5, SEQ ID NO:15.

15. A method for solubilizing a target protein, comprising: expressing a modified MBP according to claim 1 fused to a target protein so that in vivo the fusion protein is solubilized to an extent greater than can be observed for the target protein alone.

* * * * *

SEQUENCE LISTING

<160> NUMBER OF SEQ ID NOS: 40

<210> SEQ ID NO 1
<211> LENGTH: 1188
<212> TYPE: DNA
<213> ORGANISM: Escherichia coli

<400> SEQUENCE: 1

```
gcacttcacc aacaaggacc atagcatatg aaaatcgaag aaggtaaact ggtaatctgg      60
attaacggcg ataaaggcta taacggtctc gctgaagtcg gtaagaaatt cgagaaagat     120
accggaatta aagtcaccgt tgagcatccg ataaactgg aagagaaatt cccacaggtt      180
gcggcaactg gcgatggccc tgacattatc ttctgggcac acgaccgctt tggtggctac     240
gctcaatctg gcctgttggc tgaaatcacc ccggacaaag cgttccagga caagctgtat     300
ccgtttacct gggatgccgt acgttacaac ggcaagctga ttgcttaccc gatcgctgtt     360
gaagcgttat cgctgattta aacaaagat ctgctgccga acccgccaaa aacctgggaa      420
gagatcccgg cgctggataa agaactgaaa gcgaaaggta gagcgcgct gatgttcaac      480
ctgcaagaac cgtacttcac ctggccgctg attgctgctg acggggtta tgcgttcaag     540
tatgaaaacg gcaagtacga cattaaagac gtgggcgtgg ataacgctgg cgcgaaagcg     600
ggtctgacct tcctggttga cctgattaaa aacaaacaca tgaatgcaga caccgattac     660
tccatcgcag aagctgcctt taataaaggc gaaacagcga tgaccatcaa cggcccgtgg    720
gcatggtcca acatcgacac cagcaaagtg aattatggtg taacggtact gccgaccttc    780
aagggtcaac catccaaacc gttcgttggc gtgctgagcg caggtattaa cgccgccagt    840
ccgaacaaag agctggcaaa agagttcctc gaaaactatc tgctgactga tgaaggtctg    900
gaagcggtta taaagacaa accgctgggt gccgtagcgc tgaagtctta cgaggaagag    960
ttggcgaaag atccacgtat tgccgccact atggaaaacg cccagaaagg tgaaatcatg   1020
ccgaacatcc gcagatgtc cgcttctctgg tatgccgtgc gtactgcggt gatcaacgcc   1080
gccagcggtc gtcagactgt cgatgaagcc ctgaaagacg cgcagactaa ttcgagctcg   1140
aacaacaaca acaataacaa taacaacaac ctcgggatcg agggaagg                1188
```

<210> SEQ ID NO 2
<211> LENGTH: 387
<212> TYPE: PRT
<213> ORGANISM: artificial
<220> FEATURE:
<223> OTHER INFORMATION: wild-type maltose-binding protein from pMAL-c2X

<400> SEQUENCE: 2

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95
```

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
370                 375                 380

Glu Gly Arg
385

<210> SEQ ID NO 3
<211> LENGTH: 1188
<212> TYPE: DNA
<213> ORGANISM: Escherichia coli

<400> SEQUENCE: 3
gcacttcacc aacaaggacc atagcatatg aaaatcgaag aaggtaaact ggtaatctgg      60
attaacggcg ataaaggcta taacggtctc gctgaagtcg gtaagaaatt cgagaaagat     120
accggaatta aagtcaccgt tgagcatccg gataaactgg aagagaaatt cccacaggtt     180
gcggcaactg cgatggccc tgacattatc ttctgggcac acgaccgctt tggtggctac     240
gctcaatctg gcctgttggc tgaaatcacc ccggacaaag cgttccagga caagctgtat     300
ccgtttacct gggatgccgt acgttacaac ggcaagctga ttgcttaccc gatcgctgtt     360
gaagcgttat cgctgattta taacaaagat ctgctgccga cccgccaaa acctgggaa      420 gagatcccgg cgctggataa agaactgaaa gcgaaggta agagcgcgct gatgttcaac     480

```
ctgcaagaac cgtacttcac ctggccgctg attgctgctg acgggggtta tgcgttcaag    540
tatgaaaacg gcaagtacga cattaaagac gtgggcgtgg ataacgctgg cgcgaaagcg    600
ggtctgacct tcctggttga cctgattaaa aacaaacaca tgaatgcaga caccgattac    660
tccatcgcag aagctgcctt taataaaggc gaaacagcga tgaccatcaa cggcccgtgg    720
gcatggtcca acatcgacac cagcaaagtg aattatggtg taacggtact gccgaccttc    780
aagggtcaac atccaaaacc gttcgttggc gtgctgagcg caggtattaa cgccgccagt    840
ccgaacaaag agctggcaaa agagttcctc gaaaactatc tgctgactga tgaaggtctg    900
gaagcggtta ataagacaa accgctgggt gccgtagcgc tgaagtctta cgaggaagag    960
ttggtgaaag atccacgtat tgccgccact atggaaaacg cccagaaagg tgaaatcatg   1020
ccgaacatcc cgcagatgtc cgctttctgg tatgccgtgc gtactgcggt gatcaacgcc   1080
gccagcggtc gtcagactgt cgatgaagcc ctgaaagacg cgcagactaa ttcgagctcg   1140
aacaacaaca caataacaa taacaacaac ctcgggatcg agggaagg               1188
```

<210> SEQ ID NO 4
<211> LENGTH: 387
<212> TYPE: PRT
<213> ORGANISM: Escherichia coli

<400> SEQUENCE: 4

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Leu Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255
```

```
Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
            290                 295                 300

Leu Lys Ser Tyr Glu Glu Leu Val Lys Asp Pro Arg Ile Ala Ala
305                 310                 315                 320

Thr Met Glu Asn Ala Gln Lys Gly Glu Ile Met Pro Asn Ile Pro Gln
                    325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Leu Gly Ile
            370                 375                 380

Glu Gly Arg
385
```

<210> SEQ ID NO 5
<211> LENGTH: 1188
<212> TYPE: DNA
<213> ORGANISM: Escherichia coli

<400> SEQUENCE: 5

```
gcacttcacc aacaaggacc atagcatatg aaaatcgaag aaggtaaaact ggtaatctgg     60
attaacggcg ataaaggcta taacggtctc gctgaagtcg gtaagaaatt cgagaaagat    120
accggaatta aagtcaccgt tgagcatccg gataaactgg aagagaaatt cccacaggtt    180
gcggcaactg cgatggccct tgacattatc ttctgggcac acgaccgctt tggtggctac    240
gctcaatctg gcctgttggc tgaaatcacc ccggacaaag cgttccagga caagctgtat    300
ccgtttacct gggatgccgt acgttacaac ggcaagctga ttgcttaccc gatcgctgtt    360
gaagcgttat cgctgattta taacaaagat ctgctgccga cccgccaaa acctgggaa     420
gagatcccgg cgctggataa agaactgaaa gcgaaaggta agaccgcgct gatgttcaac    480
ctgcaagaac cgtacttcac ctggccgctg attgctgctg acggggtta tgcgttcaag    540
tatgaaaacg gcaagtacga cattaaagac gtgggcgtgg ataacgctgg cgcgaaagcg    600
ggtctgacct tcctggttga cctgattaaa acaaacaca tgaatgcaga caccgattac    660
tccatcgcag aagctgcctt taataaaggc gaaacagcga tgaccatcaa cggcccgtgg    720
gcatggtcca acatcgacac cagcaaagtg aattatggtg taacggtact gccgaccttc    780
aagggtcaac catccaaacc gttcgttggc gtgctgagcg caggtattaa cgccgccagt    840
ccgaacaaag agctggcaaa agagttcctc gaaaactatc tgctgactga tgaaggtctg    900
gaagcggtta ataaagacaa accgctgggt gccgtagcgc tgaagtctta cgaggaagag    960
ttggcgaaaa tcacgtat tgccgccact atggaaaacg cccagaaagg tgaaatcatg    1020
ccgaacatcc cgcagatgtc cgctttctgg tatgccgtgc gtactgcggt gatcaacgcc    1080
gccagcggtc gtcagactgt cgatgaagcc ctgaaagacg cgcagactaa ttcgagctcg   1140
aacaacaaca acaataacaa taacaacaac ctcgggatcg agggaagg                 1188
```

<210> SEQ ID NO 6
<211> LENGTH: 387
<212> TYPE: PRT

-continued

<213> ORGANISM: Escherichia coli

<400> SEQUENCE: 6

```
Met Lys Ile Glu Glu Gly Lys Leu Val Ile Trp Ile Asn Gly Asp Lys
  1               5                  10                  15

Gly Tyr Asn Gly Leu Ala Glu Val Gly Lys Lys Phe Glu Lys Asp Thr
             20                  25                  30

Gly Ile Lys Val Thr Val Glu His Pro Asp Lys Leu Glu Glu Lys Phe
         35                  40                  45

Pro Gln Val Ala Ala Thr Gly Asp Gly Pro Asp Ile Ile Phe Trp Ala
     50                  55                  60

His Asp Arg Leu Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
130                 135                 140

Lys Thr Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg
385
```

<210> SEQ ID NO 7
<211> LENGTH: 1188
<212> TYPE: DNA
<213> ORGANISM: Escherichia coli

<400> SEQUENCE: 7

```
gcacttcacc aacaaggacc atagcatatg aaaatcgaag aaggtaaact ggtaatctgg      60
attaacggcg ataaaggcta taacggtctc gctgaagtcg gtaagaaatt cgagaaagat     120
accggaatta aagtcaccgt tgagcatccg dataaactgg aagagaaatt cccacaggtt     180
gcggcaactg gcgatggccc tgacattatc ttctgggcac acgaccgcct tggtggctac     240
gctcaatctg gcctgttggc tgaaatcacc ccggacaaag cgttccagga caagctgtat     300
ccgtttacct gggatgccgt acgttacaac ggcaagctga ttgcttaccc gatcgctgtt     360
gaagcgttat cgctgattta aacaaagat ctgctgccga acccgccaaa aacctgggaa     420
gagatcccgg cgctggataa agaactgaaa gcgaaggta agagcgcgct gatgttcaac     480
ctgcaagaac cgtacttcac ctggccgctg attgctgctg acgggggtta tgcgttcaag     540
tatgaaaacg gcaagtacga cattaaagac gtgggcgtgg ataacgctgg cgcgaaagcg     600
ggtctgacct tcctggttga cctgattaaa acaaacaca tgaatgcaga caccgattac     660
tccatcgcag aagctgcctt taataaaggc gaaacagcga tgaccatcaa cggcccgtgg     720
gcatggtcca acatcgacac cagcaaagtg aattatggtg taacggtact gccgaccttc     780
aagggtcaac catccaaacc gttcgttggc gtgctgagcg caggtattaa cgccgccagt     840
ccgaacaaag agctggcaaa agagttcctc gaaaactatc tgctgactga tgaaggtctg     900
gaagcggtta ataaagacaa accgctgggt gccgtagcgc tgaagtctta cgaggaagag     960
ttggcgaaag atccacgtat tgccgccact atggaaaacg cccagaaagg tgaaatcatg    1020
ccgaacatcc gcagatgtc cgctttctgg tatgccgtgc gtactgcggt gatcaacgcc    1080
gccagcggtc gtcagactgt cgatgaagcc ctgaaagacg cgcagactaa ttcgagctcg    1140
aacaacaaca acaataacaa taacaacaac ctcgggatcg agggaagg             1188
```

<210> SEQ ID NO 8
<211> LENGTH: 387
<212> TYPE: PRT
<213> ORGANISM: Escherichia coli

<400> SEQUENCE: 8

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Leu Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly

```
         130                 135                 140
Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
                195                 200                 205

Thr Asp Tyr Ser Ile Ala Glu Ala Ala Phe Asn Lys Gly Glu Thr Ala
                210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
                275                 280                 285

Glu Gly Leu Glu Ala Val Asn Lys Asp Lys Pro Leu Gly Ala Val Ala
                290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
                355                 360                 365

Ser Ser Ser Asn Asn Asn Asn Asn Asn Asn Asn Asn Leu Gly Ile
                370                 375                 380

Glu Gly Arg
385

<210> SEQ ID NO 9
<211> LENGTH: 1188
<212> TYPE: DNA
<213> ORGANISM: Escherichia coli

<400> SEQUENCE: 9
gcacttcacc aacaaggacc atagcatatg aaaatcgaag aaggtaaact ggtaatctgg      60
attaacggcg ataaaggcta taacggtctc gctgaagtcg gtaagaaatt cgagaaagat     120
accggaatta aagtcaccgt tgagcatccg gataaactgg aagagaaatt cccacaggtt     180
gcggcaactg cgatggcccc tgacattatc ttctgggcac acgaccgctt ggtggctac     240
gctcaatctg gcctgttggc tgaaatcacc ccggacaaag cgttccagga caagctgtat     300
ccgtttacct gggatgccgt acgttacaac ggcaagctga ttgcttaccc gatcgctgtt     360
gaagcgttat cgctgattta aacaaagat ctgctgccga acccgccaaa aacctgggaa     420
gagatcccgg cgctggataa agaactgaaa gcgaaggta gagcgcgct gatgttcaac     480
ctgcaagaac cgtacttcac ctggccgctg attgctgctg acggggtta tgcgttcaag     540
tatgaaaacg gcaagtacga cattaaagac gtgggcgtgg ataacgctgg cgcgaaagcg     600
ggtctgacct tcctggttga cctgattaaa aacaaacaca tgaatgcaga caccgattac     660
```

```
tccatcgcag aagctgcctt taataaaggc gaaacagcga tgaccatcaa cggcccgtgg    720
gcatggtcca acatcgacac cagcaaagtg aattatggtg taacggtact gccgaccttc    780
aagggtcaac catccaaacc gttcgttggc gtgctgagcg caggtattaa cgccgccagt    840
ccgaacaaag agctggcaaa agagttcctc gaaaactatc tgctgactga tgaaggtctg    900
gaagcggtta ataaagacaa accgctgggt gccgtagcgc tgaagtctta cgaggaagag    960
ttggcgaaag atccacgtgt tgccgccact atggaaaacg cccagaaagg tgaaatcatg   1020
ccgaacatcc cgcagatgtc cgctttctgg tatgccgtgc gtactgcggt gatcaacgcc   1080
gccagcggtc gtcagactgt cgatgaagcc ctgaaagacg cgcagactaa ttcgagctcg   1140
aacaacaaca acaataacaa taacaacaac ctcgggatcg agggaagg                1188
```

<210> SEQ ID NO 10
<211> LENGTH: 387
<212> TYPE: PRT
<213> ORGANISM: Escherichia coli

<400> SEQUENCE: 10

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285
```

```
Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Val Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
            355                 360                 365

Ser Ser Ser Asn Asn Asn Asn Asn Asn Asn Asn Leu Gly Ile
        370                 375                 380

Glu Gly Arg
385

<210> SEQ ID NO 11
<211> LENGTH: 1188
<212> TYPE: DNA
<213> ORGANISM: Escherichia coli

<400> SEQUENCE: 11
gcacttcacc aacaaggacc atagcatatg aaaatcgaag aaggtaaact ggtaatctgg      60
attaacggcg ataaaggcta taacggtctc gctgaagtcg gtaagaaatt cgagaaagat     120
accggaatta agtcaccgt tgagcatccg gataaactgg aagagaaatt cccacaggtt      180
gcggcaactg gcgatggccc tgacattatc ttctgggcac acgaccgctt tggtggctac     240
gctcaatctg gcctgttggc tgaaatcacc ccggacaaag cgttccagga caagctgtat     300
ccgtttacct gggatgccgt acgttacaac ggcaagctga ttgcttaccc gatcgctgtt     360
gaagcgttat cgctgattta aacaaagat ctgctgccga accgccaaa aacctgggaa      420 gagatcccgg cgctggataa agaactgaaa gcgaaaggta gagcgcgct gatgttcaac      480 ctgcaagaac cgtacttcac ctggccgctg attgctgctg acggggtta tgcgttcaag     540 tatgaaaacg gcaagtacga cattaaagac gtgggcgtgg ataacgctgg cgcgaaagcg     600
ggtctgacct tcctggttga cctgattaaa acaaacaca tgaatgcaga caccgattac      660
tccatcgcag aagctgcctt taataaaggc gaaacagcga tgaccatcaa cggcccgtgg     720
gcatggtcca acatcgacac cagcaaagtg aattatggtg taacggtact gccgaccttc     780
aagggtcaac catccaaacc gttcgttggc gtgctgagcg caggtattaa cgccgccagt     840
ccgaacaaag agctggcaaa agagttcctc gaaaactatc tgctgactga tgaaggtctg     900
gaagcggtta ataaagacaa accgctgggt gccgtagcgc tgaagtctta cgaggaagag     960
ttggcgaaag atccacgtat tgccgccact atggaaaacg cccggaaagg tgaaatcatg    1020
ccgaacatcc cgcagatgtc cgcttctctg tatgccgtgc gtactgcggt gatcaacgcc    1080
gccagcggtc gtcagactgt cgatgaagcc ctgaaagacg cgcagactaa ttcgagctcg    1140
aacaacaaca caataacaa taacaacaac ctcgggatcg agggaagg                  1188

<210> SEQ ID NO 12
<211> LENGTH: 387
<212> TYPE: PRT
<213> ORGANISM: Escherichia coli

<400> SEQUENCE: 12

Met Lys Ile Glu Glu Gly Lys Leu Val Ile Trp Ile Asn Gly Asp Lys
1               5                   10                  15
```

-continued

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Arg Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg
385

<210> SEQ ID NO 13
<211> LENGTH: 1188
<212> TYPE: DNA
<213> ORGANISM: Escherichia coli

<400> SEQUENCE: 13

```
gcacttcacc aacaaggacc atagcatatg aaaatcgaag aaggtaaact ggtaatctgg      60
attaacggcg ataaaggcta taacggtctc gctgaagtcg gtaagaaatt cgagaaagat    120
accggaatta aagtcaccgt tgagcatccg gataaactgg aagagaaatt cccacaggtt    180
gcggcaactg gcgatggccc tgacattatc ttctgggcac acgaccgctt tggtggctac    240
gctcaatctg gcctgttggc tgaaatcacc ccggacaaag cgttccagga caagctgtat    300
ccgtttacct gggatgccgt acgttacaac ggcaagctga ttgcttaccc gatcgctgtt    360
gaagcgttat cgctgattta acaaagat ctgctgccga acccgccaaa aacctgggaa      420
gagatcccgg cgctggataa agaactgaaa gcgaaaggta gagcgcgct gatgttcaac      480
ctgcaagaac cgtacttcac ctggccgctg attgctgctg acggggtta tgcgttcaag     540
tatgaaaacg gcaagtacga cattaaagac gtgggcgtgg ataacgctgg cgcgaaagcg    600
ggtctgacct tcctggttga cctgattaaa aacaaacaca tgaatgcaga caccgattac    660
tccatcgcag aagctgcctt taataaaggc gaaacagcga tgaccatcaa cggcccgtgg    720
gcatggtcca acatcgacac cagcaaagtg aattatggtg taacggtact gccgaccttc    780
aagggtcaac catccaaacc gttcgttggc gtgctgagcg caggtattaa cgccgccagt    840
ccgaacaaag agctggcaaa agagttcctc gaaaactatc tgctgactga tgaaggtctg    900
gaagcggtta taaagacaa accgctgggt gccgtagcgc tgaagtctta cgaggaagag      960
ttggcgaaag atccacgtat tgccgccact atggaaaacg cccagaaagg tgaaatcatg   1020
ccgaacatcc cgcagatgtc cgctttctgg tatgccatgc gtactgcggt gatcaacgcc   1080
gccagcggtc gtcagactgt cgatgaagcc ctgaaagacg cgcagactaa ttcgagctcg   1140
aacaacaaca caataacaa taacaacaac ctcgggatcg agggaagg                1188
```

<210> SEQ ID NO 14
<211> LENGTH: 387
<212> TYPE: PRT
<213> ORGANISM: Escherichia coli

<400> SEQUENCE: 14

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175
```

```
Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Met Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg
385

<210> SEQ ID NO 15
<211> LENGTH: 1188
<212> TYPE: DNA
<213> ORGANISM: Escherichia coli

<400> SEQUENCE: 15
gcacttcacc aacaaggacc atagcatatg aaaatcgaag aaggtaaact ggtaatctgg      60
attaacggcg ataaaggcta taacggtctc gctgaagtcg gtaagaaatt cgagaaagat     120
accggaatta aagtcaccgt tgagcatccg gataaactgg aagagaaatt cccacaggtt     180
gcggcaactg gcgatggccc tgacattatc ttctgggcac acgaccgctt tggtggctac     240
gctcaatctg gcctgttggc tgaaatcacc ccggacaaag cgttccagga caagctgtat     300
ccgtttacct gggatgccgt acgttacaac ggcaagctga ttgcttaccc gatcgctgtt     360
gaagcgttat cgctgattta aacaaagat ctgctgccga acccgccaaa aacctgggaa     420
gagatcccgg cgctggataa agaactgaaa gcgaaaggta gagcgcgct gatgttcaac     480 ctgcaagaac cgtacttcac ctggccgctg attgctgctg acgggggtta tgcgttcaag     540
tatgaaaacg gcaagtacga cattaaagac gtgggcgtgg ataacgctgg cgcgaaagcg     600
ggtctgacct tcctggttga cctgattaaa aacaaacaca tgaatgcaga caccgattac     660
tccatcgcag aagctgcctt taataaaggc gaaacagcga tgaccatcaa cggcccgtgg     720
gcatggtcca acatcgacac cagcaaagtg aattatggtg taacggtact gccgaccttc     780
aagggtcaac catccaaacc gttcgttggc gtgctgagcg caggtattaa cgccgccagt     840
ccgaacaaag agctggcaaa agagttcctc gaaaactatc tgctgactga tgaaggtctg     900
```

```
gaagcggtta ataaagacaa accgctgggt gccgtagcgc tgaagtctta cgaggaagag    960
ttggcgaaag atccacgtat tgccgccact atggaaaacg cccagaaagg tgaaatcatg   1020
ccgaacatcc cgcagatgtc cgctttctgg tatgccgtgc gtactgcggt gatcaacgcc   1080
gccagcggtc gtcagactgt cgatgaagcc ctgaaagacg cgcagactaa ttcgagctca   1140
actactacca ccataactat aaccactacc ctcgggatcg agggaagg                1188
```

<210> SEQ ID NO 16
<211> LENGTH: 387
<212> TYPE: PRT
<213> ORGANISM: Escherichia coli

<400> SEQUENCE: 16

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
```

|  |  |  | 325 |  |  |  | 330 |  |  |  | 335 |
| --- | --- | --- | --- | --- | --- | --- | --- | --- | --- | --- | --- |

Met Ser Ala Phe Trp Tyr Ala Val Arg Thr Ala Val Ile Asn Ala Ala
    340       345       350

Ser Gly Arg Gln Thr Val Asp Glu Ala Leu Lys Asp Ala Gln Thr Asn
   355       360       365

Ser Ser Ser Thr Thr Thr Thr Ile Thr Ile Thr Thr Leu Gly Ile
 370       375       380

Glu Gly Arg
385

<210> SEQ ID NO 17
<211> LENGTH: 6676
<212> TYPE: DNA
<213> ORGANISM: Escherichia coli

<400> SEQUENCE: 17

| | | | | | |
|---|---|---|---|---|---|
| ccgacaccat | cgaatggtgc | aaaacctttc | gcggtatggc | atgatagcgc | ccggaagaga | 60 |
| gtcaattcag | ggtggtgaat | gtgaaaccag | taacgttata | cgatgtcgca | gagtatgccg | 120 |
| gtgtctctta | tcagaccgtt | tcccgcgtgg | tgaaccaggc | cagccacgtt | tctgcgaaaa | 180 |
| cgcgggaaaa | agtggaagcg | gcgatggcgg | agctgaatta | cattcccaac | cgcgtggcac | 240 |
| aacaactggc | gggcaaacag | tcgttgctga | ttggcgttgc | cacctccagt | ctggccctgc | 300 |
| acgcgccgtc | gcaaattgtc | gcggcgatta | atctcgcgc | cgatcaactg | ggtgccagcg | 360 |
| tggtggtgtc | gatggtagaa | cgaagcggcg | tcgaagcctg | taaagcggcg | gtgcacaatc | 420 |
| ttctcgcgca | acgcgtcagt | gggctgatca | ttaactatcc | gctggatgac | caggatgcca | 480 |
| ttgctgtgga | agctgcctgc | actaatgttc | cggcgttatt | tcttgatgtc | tctgaccaga | 540 |
| cacccatcaa | cagtattatt | ttctcccatg | aagacggtac | gcgactgggc | gtggagcatc | 600 |
| tggtcgcatt | gggtcaccag | caaatcgcgc | tgttagcggg | cccattaagt | tctgtctcgg | 660 |
| cgcgtctgcg | tctggctggc | tggcataaat | atctcactcg | caatcaaatt | cagccgatag | 720 |
| cggaacggga | aggcgactgg | agtgccatgt | ccggttttca | acaaaccatg | caaatgctga | 780 |
| atgagggcat | cgttcccact | gcgatgctgg | ttgccaacga | tcagtggcg | ctgggcgcaa | 840 |
| tgcgcgccat | taccgagtcc | gggctgcgcg | ttggtgcgga | catctcggta | gtgggatacg | 900 |
| acgataccga | agacagctca | tgttatatcc | cgccgttaac | caccatcaaa | caggattttc | 960 |
| gcctgctggg | gcaaaccagc | gtggaccgct | tgctgcaact | ctctcagggc | caggcggtga | 1020 |
| agggcaatca | gctgttgccc | gtctcactgg | tgaaaagaaa | aaccaccctg | gcgcccaata | 1080 |
| cgcaaaccgc | ctctccccgc | gcgttggccg | attcattaat | gcagctggca | cgacaggttt | 1140 |
| cccgactgga | aagcgggcag | tgagcgcaac | gcaattaatg | taagttagct | cactcattag | 1200 |
| gcacaattct | catgtttgac | agcttatcat | cgactgcacg | gtgcaccaat | gcttctggcg | 1260 |
| tcaggcagcc | atcggaagct | gtggtatggc | tgtgcaggtc | gtaaatcact | gcataattcg | 1320 |
| tgtcgctcaa | ggcgcactcc | cgttctggat | aatgttttt | gcgccgacat | cataacggtt | 1380 |
| ctggcaaata | ttctgaaatg | agctgttgac | aattaatcat | cggctcgtat | aatgtgtgga | 1440 |
| attgtgagcg | gataacaatt | tcacacagga | aacagccagt | ccgtttaggt | gttttcacga | 1500 |
| gcaattgacc | aacaaggacc | atagattatg | aaaatcgaag | aaggtaaact | ggtaatctgg | 1560 |
| attaacggcg | ataaaggcta | taacggtctc | gctgaagtcg | gtaagaaatt | cgagaaagat | 1620 |
| accggaatta | aagtcaccgt | tgagcatccg | gataaactgg | aagagaaatt | cccacaggtt | 1680 |
| gcggcaactg | gcgatggccc | tgacattatc | ttctgggcac | acgaccgctt | tggtggctac | 1740 |

```
gctcaatctg gcctgttggc tgaaatcacc ccggacaaag cgttccagga caagctgtat    1800
ccgtttacct gggatgccgt acgttacaac ggcaagctga ttgcttaccc gatcgctgtt    1860
gaagcgttat cgctgattta acaaagat ctgctgccga acccgccaaa aacctgggaa      1920
gagatcccgg cgctggataa agaactgaaa gcgaaaggta gagcgcgct gatgttcaac     1980 ctgcaagaac cgtacttcac ctggccgctg attgctgctg acggggggtta tgcgttcaag   2040 tatgaaaacg gcaagtacga cattaaagac gtgggcgtgg ataacgctgg cgcgaaagcg   2100
ggtctgacct tcctggttga cctgattaaa acaaacaca tgaatgcaga caccgattac    2160
tccatcgcag aagctgcctt taataaaggc gaaacagcga tgaccatcaa cggcccgtgg   2220
gcatggtcca acatcgacac cagcaaagtg aattatggtg taacggtact gccgaccttc   2280
aagggtcaac catccaaacc gttcgttggc gtgctgagcg caggtattaa cgccgccagt   2340
ccgaacaaag agctggcaaa agagttcctc gaaaactatc tgctgactga tgaaggtctg   2400
gaagcggtta ataaagacaa accgctgggt gccgtagcgc tgaagtctta cgaggaagag   2460
ttggcgaaag atccacgtat tgccgccact atggaaaacg cccagaaagg tgaaatcatg   2520
ccgaacatcc cgcagatgtc cgcttttctgg tatgccgtgc gtactgcggt gatcaacgcc   2580
gccagcggtc gtcagactgt cgatgaagcc ctgaaagacg cgcagactaa ttcgagctcg   2640
aacaacaaca acaataacaa taacaacaac ctcgggatcg agggaaggat ttcacatatg   2700
tccatgggcg gccgcgatat cgtcgacgga tccgaattcc ctgcaggtaa ttaaataagc    2760
ttggcactgg ccgtcgtttt acaacgtcgt gactgggaaa accctggcgt tacccaactt    2820
aatcgccttg cagcacatcc cccttttcgcc agctggcgta atagcgaaga ggcccgcacc   2880
gatcgccctt cccaacagtt gcgcagcctg aatggcgaat ggcagcttgg ctgttttggc    2940
ggatgagata agatttttcag cctgatacag attaaatcag aacgcagaag cggtctgata   3000
aaacagaatt tgcctggcgg cagtagcgcg gtggtcccac ctgaccccat gccgaactca   3060
gaagtgaaac gccgtagcgc cgatggtagt gtggggtctc cccatgcgag agtagggaac   3120
tgccaggcat caaataaaac gaaaggctca gtcgaaagac tgggcctttc gttttatctg    3180
ttgtttgtcg gtgaacgctc tcctgagtag acaaatccg ccgggagcgg atttgaacgt     3240
tgcgaagcaa cggcccggag ggtggcgggc aggacgcccg ccataaactg ccaggcatca   3300
aattaagcag aaggccatcc tgacggatgg cctttttgcg tttctacaaa ctcttttttgt    3360 ttatttttct aaatacattc aaatatgtat ccgctcatga acaataacc ctgataaatg     3420 cttcaataat attgaaaaag gaagagtatg agtattcaac atttccgtgt cgcccttatt    3480 ccctttttttg cggcattttg ccttcctgtt tttgctcacc cagaaacgct ggtgaaagta    3540
aaagatgctg aagatcagtt gggtgcacga gtgggttaca tcgaactgga tctcaacagc   3600
ggtaagatcc ttgagagttt tcgccccgaa gaacgttctc caatgatgag cacttttaaa    3660
gttctgctat gtggcgcggt attatcccgt gttgacgccg gcaagagca actcggtcgc    3720 cgcatacact attctcagaa tgacttggtt gagtactcac cagtcacaga aaagcatctt    3780
acggatggca tgacagtaag agaattatgc agtgctgcca taaccatgag tgataacact    3840
gcggccaact tacttctgac aacgatcgga ggaccgaagg agctaaccgc ttttttgcac    3900
aacatggggg atcatgtaac tcgccttgat cgttgggaac cggagctgaa tgaagccata    3960
ccaaacgacg agcgtgacac cacgatgcct gtagcaatgg caacaacgtt gcgcaaacta   4020
ttaactggcg aactacttac tctagcttcc cggcaacaat taatagactg gatggaggcg   4080
gataaagttg caggaccact tctgcgctcg gcccttccgg ctggctggtt tattgctgat    4140
```

```
aaatctggag ccggtgagcg tgggtctcgc ggtatcattg cagcactggg gccagatggt    4200 aagcccctccc gtatcgtagt tatctacacg acggggagtc aggcaactat ggatgaacga    4260
aatagacaga tcgctgagat aggtgcctca ctgattaagc attggtaact gtcagaccaa    4320
gtttactcat atatacttta gattgattta ccccggttga taatcagaaa agccccaaaa    4380
acaggaagat tgtataagca aatatttaaa ttgtaaacgt taatattttg ttaaaattcg    4440
cgttaaattt ttgttaaatc agctcatttt ttaaccaata ggccgaaatc ggcaaaatcc    4500
cttataaatc aaaagaatag accgagatag ggttgagtgt tgttccagtt tggaacaaga    4560
gtccactatt aaagaacgtg gactccaacg tcaaagggcg aaaaaccgtc tatcagggcg    4620
atggcccact acgtgaacca tcacccaaat caagtttttt ggggtcgagg tgccgtaaag    4680
cactaaatcg aaccctaaa gggagccccc gatttagagc ttgacgggga agccggcga    4740 acgtggcgag aaaggaaggg aagaaagcga aaggagcggg cgctagggcg ctggcaagtg    4800
tagcggtcac gctgcgcgta accaccacac ccgccgcgct taatgcgccg ctacagggcg    4860
cgtaaaagga tctaggtgaa gatccttttt gataatctca tgaccaaaat cccttaacgt    4920
gagttttcgt tccactgagc gtcagacccc gtagaaaaga tcaaaggatc ttcttgagat    4980
cctttttttc tgcgcgtaat ctgctgcttg caaacaaaaa aaccaccgct accagcggtg    5040
gtttgtttgc cggatcaaga gctaccaact cttttttccga aggtaactgg cttcagcaga    5100
gcgcagatac caaatactgt ccttctagtg tagccgtagt taggccacca cttcaagaac    5160
tctgtagcac cgcctacata cctcgctctg ctaatcctgt taccagtggc tgctgccagt    5220
ggcgataagt cgtgtcttac cgggttggac tcaagacgat agttaccgga taaggcgcag    5280
cggtcgggct gaacggggg ttcgtgcaca cagcccagct tggagcgaac gacctacacc    5340
gaactgagat acctacagcg tgagctatga gaaagcgcca cgcttcccga agggagaaag    5400
gcggacaggt atccggtaag cggcagggtc ggaacaggag agcgcacgag ggagcttcca    5460
gggggaaacg cctggtatct ttatagtcct gtcgggtttc gccacctctg acttgagcgt    5520
cgatttttgt gatgctcgtc aggggggcgg agcctatgga aaaacgccag caacgcggcc    5580 ttttttacggt tcctggcctt ttgctggcct tttgctcaca tgttctttcc tgcgttatcc    5640
cctgattctg tggataaccg tattaccgcc tttgagtgag ctgataccgc tcgccgcagc    5700
cgaacgaccg agcgcagcga gtcagtgagc gaggaagcgg aagagcgcct gatgcggtat    5760 tttctccta cgcatctgtg cggtatttca caccgcatat atggtgcact ctcagtacaa    5820
tctgctctga tgccgcatag ttaagccagt atacactccg ctatcgctac gtgactgggt    5880
catggctgcg ccccgacacc cgccaacacc cgctgacgcg ccctgacggg cttgtctgct    5940
cccggcatcc gcttacagac aagctgtgac cgtctccggg agctgcatgt gtcagaggtt    6000
ttcaccgtca tcaccgaaac gcgcgaggca gctgcggtaa agctcatcag cgtggtcgtg    6060
cagcgattca cagatgtctg cctgttcatc cgcgtccagc tcgttgagtt tctccagaag    6120
cgttaatgtc tggcttctga taaagcgggc catgttaagg gcggtttttt cctgtttggt    6180
cactgatgcc tccgtgtaag ggggatttct gttcatgggg gtaatgatac cgatgaaacg    6240
agagaggatg ctcacgatac gggttactga tgatgaacat gcccggttac tggaacgttg    6300
tgagggtaaa caactggcgg tatggatgcg gcgggaccag agaaaaatca ctcagggtca    6360
atgccagcgc ttcgttaata cagatgtagg tgttccacag ggtagccagc agcatcctgc    6420
gatgcagatc cggaacataa tggtgcaggg cgctgacttc cgcgtttcca gactttacga    6480
aacacggaaa ccgaagacca ttcatgttgt tgctcaggtc gcagacgttt tgcagcagca    6540
```

-continued

```
gtcgcttcac gttcgctcgc gtatcggtga ttcattctgc taaccagtaa ggcaaccccg    6600
ccagcctagc cgggtcctca acgacaggag cacgatcatg cgcacccgtg gccaggaccc    6660
aacgctgccc gaaatt                                                    6676

<210> SEQ ID NO 18
<211> LENGTH: 5677
<212> TYPE: DNA
<213> ORGANISM: Escherichia coli

<400> SEQUENCE: 18
ccgacaccat cgaatggtgc aaaacctttc gcggtatggc atgatagcgc ccggaagaga      60
gtcaattcag ggtggtgaat gtgaaaccag taacgttata cgatgtcgca gagtatgccg     120
gtgtctctta tcagaccgtt tcccgcgtgg tgaaccaggc cagccacgtt tctgcgaaaa     180
cgcgggaaaa agtggaagcg gcgatggcgg agctgaatta cattcccaac cgcgtggcac     240
aacaactggc gggcaaacag tcgttgctga ttggcgttgc cacctccagt ctggccctgc     300
acgcgccgtc gcaaattgtc gcggcgatta atctcgcgc cgatcaactg ggtgccagcg     360
tggtggtgtc gatggtagaa cgaagcggcg tcgaagcctg taaagcggcg gtgcacaatc     420
ttctcgcgca acgcgtcagt gggctgatca ttaactatcc gctggatgac caggatgcca     480
ttgctgtgga agctgcctgc actaatgttc cggcgttatt tcttgatgtc tctgaccaga     540
cacccatcaa cagtattatt ttctcccatg aagacggtac gcgactgggc gtggagcatc     600
tggtcgcatt gggtcaccag caaatcgcgc tgttagcggg cccattaagt tctgtctcgg     660
cgcgtctgcg tctggctggc tggcataaat atctcactcg caatcaaatt cagccgatag     720
cggaacggga aggcgactgg agtgccatgt ccggttttca acaaaccatg caaatgctga     780
atgagggcat cgttcccact gcgatgctgg ttgccaacga tcagatggcg ctgggcgcaa     840
tgcgcgccat taccgagtcc gggctgcgcg ttggtgcgga tatttcggta gtgggatacg     900
acgataccga agacagctca tgttatatcc gccgttaac caccatcaaa caggattttc     960
gcctgctggg gcaaaccagc gtggaccgct tgctgcaact ctctcagggc caggcggtga    1020
agggcaatca gctgttgccc gtctcactgg tgaaaagaaa aaccaccctg gcgcccaata    1080
cgcaaaccgc ctctccccgc gcgttggccg attcattaat gcagctggca cgacaggttt    1140
cccgactgga aagcgggcag tgagcgcaac gcaattaatg taagttagct cactcattag    1200
gcacaattct catgtttgac agcttatcat cgactgcacg gtgcaccaat gcttctggcg    1260
tcaggcagcc atcggaagct gtggtatggc tgtgcaggtc gtaaatcact gcataattcg    1320
tgtcgctcaa ggcgcactcc cgttctggat aatgttttt gcgccgacat cataacggtt    1380
ctggcaaata ttctgaaatg agctgttgac aattaatcat cggctcgtat aatgtgtgga    1440
attgtgagcg gataacaatt tcacacagga acagccagt ccgtttaggt gttttcacga    1500
gcaattgacc aacaaggacc atagattatg aaaatcgaag aaggtaaact ggtaatctgg    1560
attaacggcg ataaaggcta taacggtctc gctgaagtcg gtaagaaatt cgagaaagat    1620
accggaatta aagtcaccgt tgagcatccg gataaactgg aagagaaatt cccacaggtt    1680
gcggcaactg gcgatggccc tgacattatc ttctgggcac acgaccgctt tggtggctac    1740
gctcaatctg gcctgttggc tgaaatcacc ccggacaaag cgttccagga caagctgtat    1800
ccgtttacct gggatgccgt acgttacaac ggcaagctga ttgcttaccc gatcgctgtt    1860
gaagcgttat cgctgattta taacaaagat ctgctgccga accgccaaa aacctgggaa    1920 gagatcccgg cgctggataa agaactgaaa gcgaaaggta agagcgcgct gatgttcaac    1980
```

```
ctgcaagaac cgtacttcac ctggccgctg attgctgctg acgggggtta tgcgttcaag    2040
tatgaaaacg gcaagtacga cattaaagac gtgggcgtgg ataacgctgg cgcgaaagcg    2100
ggtctgacct tcctggttga cctgattaaa aacaaacaca tgaatgcaga caccgattac    2160
tccatcgcag aagctgcctt taataaaggc gaaacagcga tgaccatcaa cggcccgtgg    2220
gcatggtcca acatcgacac cagcaaagtg aattatggtg taacggtact gccgaccttc    2280
aagggtcaac catccaaacc gttcgttggc gtgctgagcg caggtattaa cgccgccagt    2340
ccgaacaaag agctggcaaa agagttcctc gaaaactatc tgctgactga tgaaggtctg    2400
gaagcggtta taaagacaa accgctgggt gccgtagcgc tgaagtctta cgaggaagag    2460
ttggtgaaag atccgcggat tgccgccact atggaaaacg cccagaaagg tgaaatcatg    2520
ccgaacatcc cgcagatgtc cgctttctgg tatgccgttc gaactgcggt gatcaacgcc    2580
gccagcggtc gtcagactgt cgatgaagcc ctgaagacg cgcagactaa ttcgagctcg    2640
aacaacaaca caataacaa taacaacaac ctcgggatcg agggaaggat ttcacatatg    2700
tccatgggcg gccgcgatat cgtcgacgga tccgaattcc ctgcaggtaa ttaaataagc    2760
ttcaaataaa acgaaaggct cagtcgaaag actgggcctt tcgttttatc tgttgtttgt    2820
cggtgaacgc tctcctgagt aggacaaatc cgccgggagc ggatttgaac gttgcgaagc    2880
aacggcccgg agggtggcgg gcaggacgcc cgccataaac tgccaggcat caaattaagc    2940
agaaggccat cctgacggat ggcctttttg cgtttctaca aactctttcg gtccgttgtt    3000
tatttttcta aatacattca aatatgtatc cgctcatgag acaataaccc tgataaatgc    3060
ttcaataata ttgaaaaagg aagagtatga gtattcaaca tttccgtgtc gcccttattc    3120 cctttttgc ggcattttgc cttcctgttt ttgctcaccc agaaacgctg gtgaaagtaa    3180
aagatgctga agatcagttg ggtgcacgag tgggttacat cgaactggat ctcaacagcg    3240
gtaagatcct tgagagtttt cgccccgaag aacgttttcc aatgatgagc acttttaaag    3300
ttctgctatg tggcgcggta ttatcccgtg ttgacgccgg gcaagagcaa ctcggtcgcc    3360
acatacacta ttctcagaat gacttggttg agtactcacc agtcacagaa aagcatctta    3420
cggatggcat gacagtaaga gaattatgca gtgctgccat aaccatgagt gataacactg    3480
cggccaactt acttctgaca acgatcggag gaccgaagga gctaaccgct ttttgcaca    3540 acatggggga tcatgtaact cgccttgatc gttgggaacc ggagctgaat gaagccatac    3600
caaacgacga gcgtgacacc acgatgcctg tagcaatggc aacaacgttg cgcaaactat    3660
taactggcga actacttact ctagcttccc ggcaacaatt aatagactgg atggaggcgg    3720
ataaagttgc aggaccactt ctgcgctcgg cccttccggc tggctggttt attgctgata    3780
aatctggagc cggtgagcgt gggtctcgcg gtatcattgc agcactgggg ccagatggta    3840
agccctcccg tatcgtagtt atctacacga cggggagtca ggcaactatg gatgaacgaa    3900
atagacagat cgctgagata ggtgcctcac tgattaagca ttggtaactg tcagaccaag    3960
tttactcata tatactttag attgatttcc ttaggactga gcgtcaaccc cgtagaaaag    4020
atcaaaggat cttcttgaga tcctttttt ctgcgcgtaa tctgctgctt gcaaacaaaa    4080
aaaccaccgc taccagcggt ggtttgtttg ccggatcaag agctaccaac tcttttttccg    4140 aaggtaactg gcttcagcag agcgcagata ccaaatactg tccttctagt gtagccgtag    4200
ttaggccacc acttcaagaa ctctgtagca ccgcctacat acctcgctct gctaatcctg    4260
ttaccagtgg ctgctgccag tggcgataag tcgtgtctta ccgggttgga ctcaagacga    4320
tagttaccgg ataaggcgca gcggtcgggc tgaacggggg gttcgtgcac acagcccagc    4380
```

```
ttggagcgaa cgacctacac cgaactgaga tacctacagc gtgagctatg agaaagcgcc      4440
acgcttcccg aagggagaaa ggcggacagg tatccggtaa gcggcagggt cggaacagga      4500
gagcgcacga gggagcttcc aggggggaaac gcctggtatc tttatagtcc tgtcgggttt      4560
cgccacctct gacttgagcg tcgatttttg tgatgctcgt cagggggggcg gagcctatgg      4620 aaaaacgcca gcaacgcggc cttttttacgg ttcctggcct tttgctggcc ttttgctcac      4680
atgttctttc ctgcgttatc ccctgattct gtggataacc gtattaccgc ctttgagtga      4740
gctgataccg ctcgccgcag ccgaacgacc gagcgcagcg agtcagtgag cgaggaagcg      4800 gaaagagcgcc tgatgcggta ttttctcctt acgcatctgt gcggtatttc acaccgcata      4860
taaggtgcac tgtgactggg tcatggctgc gccccgacac ccgccaacac ccgctgacgc      4920
gccctgacgg gcttgtctgc tcccggcatc cgcttacaga caagctgtga ccgtctccgg      4980
gagctgcatg tgtcagaggt tttcaccgtc atcaccgaaa cgcgcgaggc agctgcggta      5040
aagctcatca gcgtggtcgt gcagcgattc acagatgtct gcctgttcat ccgcgtccag      5100
ctcgttgagt ttctccagaa gcgttaatgt ctggcttctg ataaagcggg ccatgttaag      5160
ggcggttttt tcctgtttgg tcactgatgc ctccgtgtaa gggggatttc tgttcatggg      5220
ggtaatgata ccgatgaaac gagagaggat gctcacgata cgggttactg atgatgaaca      5280
tgcccggtta ctggaacgtt gtgagggtaa acaactggcg gtatggatgc ggcgggacca      5340
gagaaaaatc actcagggtc aatgccagcg cttcgttaat acagatgtag gtgttccaca      5400
gggtagccag cagcatcctg cgatgcagat ccggaacata atggtgcagg gcgctgactt      5460
ccgcgtttcc agactttacg aaacacggaa accgaagacc attcatgttg ttgctcaggt      5520
cgcagacgtt ttgcagcagc agtcgcttca cgttcgctcg cgtatcggtg attcattctg      5580
ctaaccagta aggcaacccc gccagcctag ccgggtcctc aacgacagga gcacgatcat      5640
gcgcacccgt ggccaggacc caacgctgcc cgaaatt                              5677
```

<210> SEQ ID NO 19
<211> LENGTH: 30
<212> TYPE: DNA
<213> ORGANISM: artificial
<220> FEATURE:
<223> OTHER INFORMATION: oligonucleotide

<400> SEQUENCE: 19

```
ggagacauga attcaatgaa aatcgaagaa                                        30
```

<210> SEQ ID NO 20
<211> LENGTH: 30
<212> TYPE: DNA
<213> ORGANISM: artificial
<220> FEATURE:
<223> OTHER INFORMATION: oligonucleotide

<400> SEQUENCE: 20

```
gggaaaguaa gcttaatcct tccctcgatc                                        30
```

<210> SEQ ID NO 21
<211> LENGTH: 49
<212> TYPE: DNA
<213> ORGANISM: artificial
<220> FEATURE:
<223> OTHER INFORMATION: oligonucleotide

<400> SEQUENCE: 21

```
gactcatatg aaaatcgaag aaggtaaact ggtaatctgg attaacggc                   49
```

```
<210> SEQ ID NO 22
<211> LENGTH: 33
<212> TYPE: DNA
<213> ORGANISM: artificial
<220> FEATURE:
<223> OTHER INFORMATION: oligonucleotide

<400> SEQUENCE: 22
atataagctt tcaccttccc tcgatcccga ggt                              33

<210> SEQ ID NO 23
<211> LENGTH: 24
<212> TYPE: DNA
<213> ORGANISM: artificial
<220> FEATURE:
<223> OTHER INFORMATION: oligonucleotide

<400> SEQUENCE: 23
cttcaagggt caaccatcca aacc                                        24

<210> SEQ ID NO 24
<211> LENGTH: 27
<212> TYPE: DNA
<213> ORGANISM: artificial
<220> FEATURE:
<223> OTHER INFORMATION: oligonucleotide

<400> SEQUENCE: 24
aatacgcgga tctttcacca actcttc                                     27

<210> SEQ ID NO 25
<211> LENGTH: 27
<212> TYPE: DNA
<213> ORGANISM: artificial
<220> FEATURE:
<223> OTHER INFORMATION: oligonucleotide

<400> SEQUENCE: 25
gaagagttgg tgaaagatcc gcgtatt                                     27

<210> SEQ ID NO 26
<211> LENGTH: 28
<212> TYPE: DNA
<213> ORGANISM: artificial
<220> FEATURE:
<223> OTHER INFORMATION: oligonucleotide

<400> SEQUENCE: 26
ctgagaattc tgaaatcctt ccctcgat                                    28

<210> SEQ ID NO 27
<211> LENGTH: 24
<212> TYPE: DNA
<213> ORGANISM: artificial
<220> FEATURE:
<223> OTHER INFORMATION: oligonucleotide

<400> SEQUENCE: 27
cacgagcaat tgaccaacaa ggac                                        24

<210> SEQ ID NO 28
<211> LENGTH: 24
<212> TYPE: DNA
<213> ORGANISM: artificial
<220> FEATURE:
<223> OTHER INFORMATION: oligonucleotide
```

```
<400> SEQUENCE: 28
gatcgagagc tcgaattagt ctgc                                              24

<210> SEQ ID NO 29
<211> LENGTH: 24
<212> TYPE: DNA
<213> ORGANISM: artificial
<220> FEATURE:
<223> OTHER INFORMATION: oligonucleotide

<400> SEQUENCE: 29
ccgaccttca agggtcaacc atcc                                              24

<210> SEQ ID NO 30
<211> LENGTH: 24
<212> TYPE: DNA
<213> ORGANISM: artificial
<220> FEATURE:
<223> OTHER INFORMATION: oligonucleotide

<400> SEQUENCE: 30
ccgcagtacg catggcatac caga                                              24

<210> SEQ ID NO 31
<211> LENGTH: 24
<212> TYPE: DNA
<213> ORGANISM: artificial
<220> FEATURE:
<223> OTHER INFORMATION: oligonucleotide

<400> SEQUENCE: 31
tctggtatgc catgcgtact gcgg                                              24

<210> SEQ ID NO 32
<211> LENGTH: 24
<212> TYPE: DNA
<213> ORGANISM: artificial
<220> FEATURE:
<223> OTHER INFORMATION: oligonucleotide

<400> SEQUENCE: 32
cgccagggtt ttcccagtca cgac                                              24

<210> SEQ ID NO 33
<211> LENGTH: 33
<212> TYPE: DNA
<213> ORGANISM: artificial
<220> FEATURE:
<223> OTHER INFORMATION: oligonucleotide

<400> SEQUENCE: 33
caactactac caccataact ataaccacta ccc                                    33

<210> SEQ ID NO 34
<211> LENGTH: 41
<212> TYPE: DNA
<213> ORGANISM: artificial
<220> FEATURE:
<223> OTHER INFORMATION: oligonucleotide

<400> SEQUENCE: 34
ccgagggtag tggttatagt tatggtggta gtagttgagc t                           41

<210> SEQ ID NO 35
<211> LENGTH: 52
<212> TYPE: DNA
```

```
<213> ORGANISM: artificial
<220> FEATURE:
<223> OTHER INFORMATION: oligonucleotide

<400> SEQUENCE: 35
actaccctcg ggatcgaggg aaggggtacg cttgaaggtt ctcagcatgc ac        52

<210> SEQ ID NO 36
<211> LENGTH: 24
<212> TYPE: DNA
<213> ORGANISM: artificial
<220> FEATURE:
<223> OTHER INFORMATION: oligonucleotide

<400> SEQUENCE: 36
ggtcgtcaga ctgtcgatga agcc                                       24

<210> SEQ ID NO 37
<211> LENGTH: 25
<212> TYPE: DNA
<213> ORGANISM: artificial
<220> FEATURE:
<223> OTHER INFORMATION: oligonucleotide

<400> SEQUENCE: 37
agatccgcgg gttgccgcca ctatg                                      25

<210> SEQ ID NO 38
<211> LENGTH: 99
<212> TYPE: DNA
<213> ORGANISM: artificial
<220> FEATURE:
<223> OTHER INFORMATION: oligonucleotide

<400> SEQUENCE: 38
gcagttcgaa cggcatacca gaaagcggac atctgcggga tgttcggcat gatttcacct    60
ttctgggcgt tttccatagt ggcggcaacc cgcggatct                           99

<210> SEQ ID NO 39
<211> LENGTH: 25
<212> TYPE: DNA
<213> ORGANISM: artificial
<220> FEATURE:
<223> OTHER INFORMATION: oligonucleotide

<400> SEQUENCE: 39
agatccgcgg gcagccgcca ctatg                                      25

<210> SEQ ID NO 40
<211> LENGTH: 99
<212> TYPE: DNA
<213> ORGANISM: artificial
<220> FEATURE:
<223> OTHER INFORMATION: oligonucleotide

<400> SEQUENCE: 40
gcagttcgaa cggcatacca gaaagcggac atctgcggga tgttcggcat gatttcacct    60
ttctgggcgt tttccatagt ggcggctgcc cgcggatct                           99
```